United States Patent [19]

Lawlis

[11] Patent Number: 6,130,063
[45] Date of Patent: *Oct. 10, 2000

[54] DNA SEQUENCES, VECTORS, AND FUSION POLYPEPTIDES TO INCREASE SECRETION OF DESIRED POLYPEPTIDES FROM FILAMENTOUS FUNGI

[75] Inventor: Virgil Bryan Lawlis, San Mateo, Calif.

[73] Assignee: Genencor International, Inc., Palo Alto, Calif.

[*] Notice: This patent is subject to a terminal disclaimer.

[21] Appl. No.: 08/828,152

[22] Filed: Mar. 27, 1997

Related U.S. Application Data

[63] Continuation of application No. 08/318,491, Oct. 5, 1994, Pat. No. 5,679,543, which is a continuation of application No. 08/207,805, Mar. 7, 1994, abandoned, which is a continuation of application No. 07/794,603, Nov. 15, 1991, abandoned, which is a continuation of application No. 07/369,698, Jun. 16, 1989, abandoned, which is a continuation-in-part of application No. 07/163,219, Feb. 26, 1988, abandoned, which is a continuation of application No. 06/882,224, Jul. 7, 1986, abandoned, which is a continuation-in-part of application No. 06/771,374, Aug. 29, 1985, abandoned.

[51] Int. Cl.[7] .............................. C12N 15/00; C12N 1/15; C12N 1/19; C07H 21/04
[52] U.S. Cl. ..................... 435/69.1; 435/69.1; 435/69.7; 435/254.11; 435/254.3; 435/254.4; 435/254.5; 435/254.6; 435/320.1; 530/350; 536/23.1; 536/23.4
[58] Field of Search .................... 435/69.1, 69.7, 435/69.8, 71.1, 463, 205, 254.11, 320.1, 254.3, 254.4, 254.5, 254.6; 530/350; 536/23.1, 23.4, 24.1

[56] References Cited

U.S. PATENT DOCUMENTS 5,679,543  10/1997  Lawlis ..................................... 435/69.1

OTHER PUBLICATIONS

Innes et al., "Expression, Glycosylation, and Secretion of an Aspergillus Glucoamylase by *Saccharomyces cerevisiae*," *Science*, 228:21–228 (1985).
Sidhu and Bollon, "Analysis of α–Factor Secretion Signals by Fusing with Acid Phosphatase of Yeast," *Gene*, 54:175–184 (1987).
Rothblatt et al., "Secretion in Yeast: Structural Features Influencing the Post–Translational Translocation of Prepro–α–Factor in vitro," *The EMBO Journal*, 6(11):3455–3463 (1987).
Buell et al., "Optimizing the Expression in *E. coli* of a Synthetic Gene Encoding Somatomedin–C (IGF–I)," *Nucleic Acids Research*, 13(6):1923–1938 (1985).
Mellor et al., "Efficient Synthesis of Enzymatically Active Calf Chymosin in *Saccharomyces cerevisiae*," *Gene*, 24:1–14 (1983).
Harris et al., "Molecular Cloning and Nucleotide Sequence of cDNA Coding for Calf Preprochymosin," *Nucleic Acids Research*, 10:2177–2187 (1982).
Knowles et al., "The Cellulase Gene of Trichoderma," *Antonie van Leeuwenhoek Journal of Microbiology*, 53(5):335–341 (1987).

*Primary Examiner*—David Guzo
*Assistant Examiner*—Mark L. Shibuya
*Attorney, Agent, or Firm*—Flehr Hohbach Test Albritton & Herbert LLP; Richard F. Trecartin, Esq.; Robin M. Silva, Esq.

[57] ABSTRACT

The invention includes novel fusion DNA sequences encoding fusion polypeptides which when expressed in a filamentous fungus result in the expression of fusion polypeptides which when secreted result in increased levels of secretion of the desired polypeptide as compared to the expression and secretion of such polypeptides from filamentous fungi transformed with previously used DNA sequences. The fusion DNA sequences comprise from the 5' terminus four DNA sequences which encode a fusion polypeptide comprising, from the amino to carbonyl-terminus, first, second, third and fourth amino acid sequences. The first DNA sequence encodes a signal peptide functional as a secretory sequence in a first filamentous fungus. The second DNA sequence encodes a secreted polypeptide or portion thereof which is normally secreted from the same filamentous fungus or a second filamentous fungus. The third DNA sequence encodes a cleavable linker polypeptide while the fourth DNA sequence encodes a desired polypeptide. When the fusion DNA sequence is expressed either in the first or second filamentous fungus, increased secretion of the desired polypeptide is obtained as compared to that which is obtained when the desired polypeptide is expressed from DNA sequences encoding a fusion polypeptide which does not contain the second polypeptide normally secreted from either of the filamentous fungi.

41 Claims, 14 Drawing Sheets

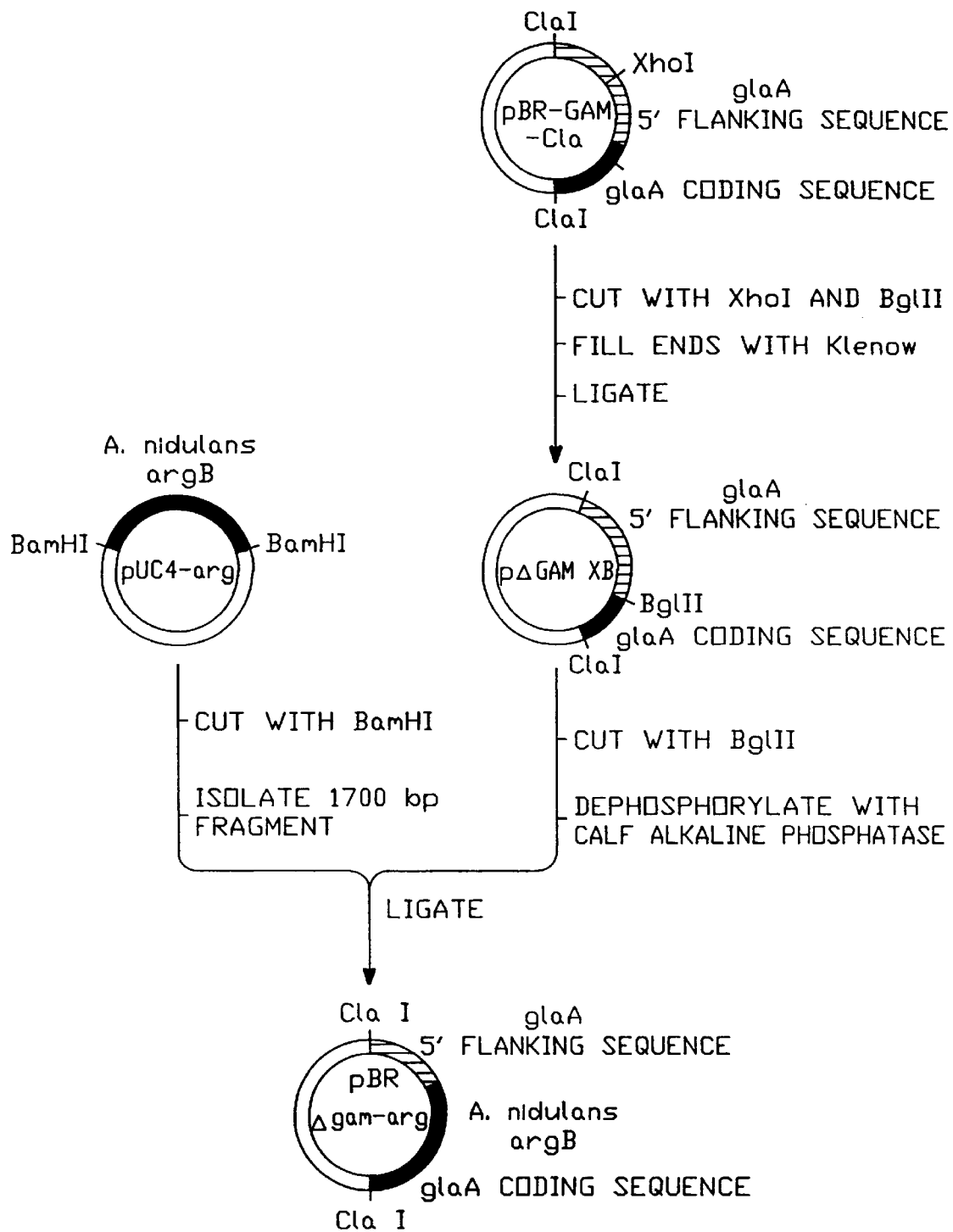
FIG._1

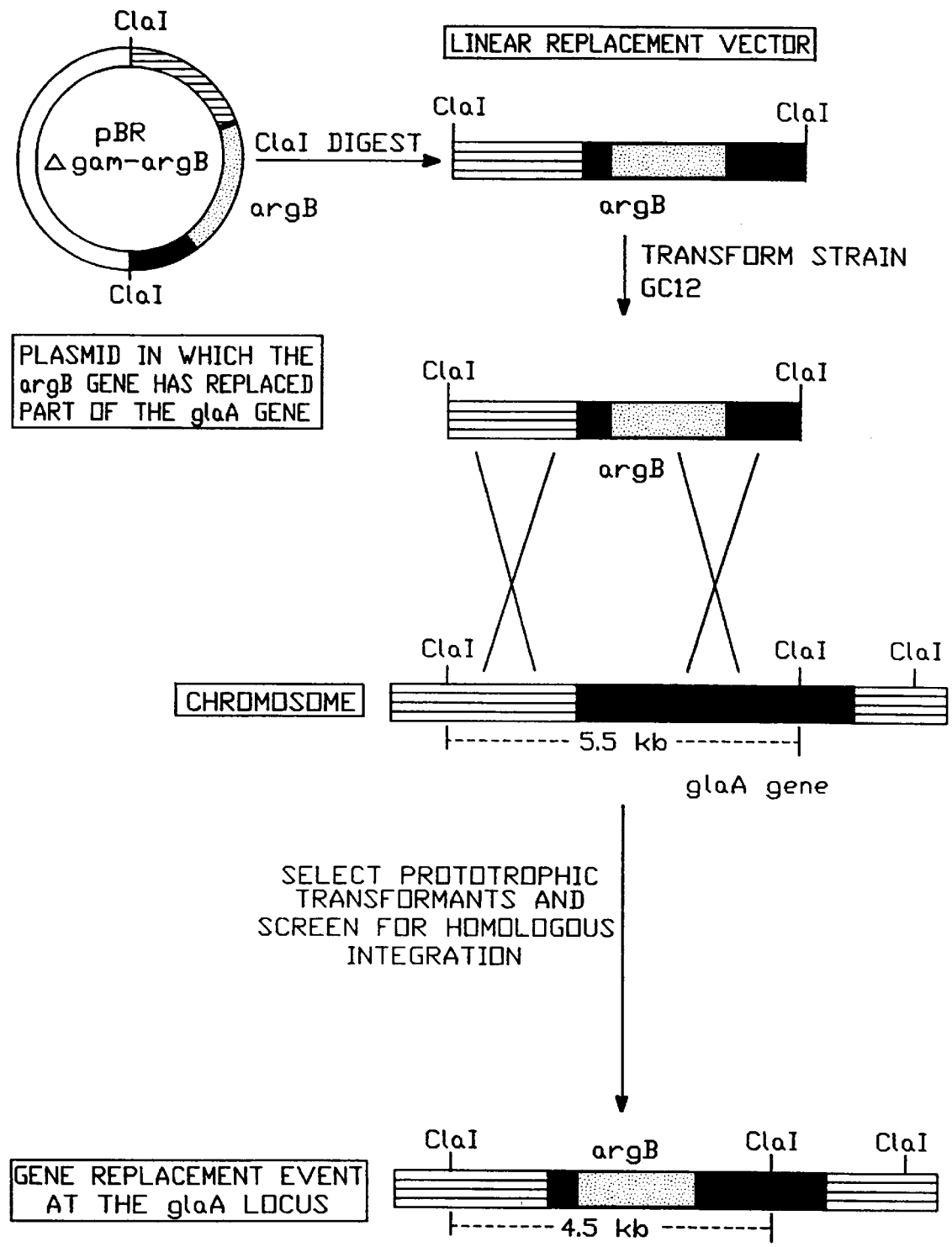
FIG._2

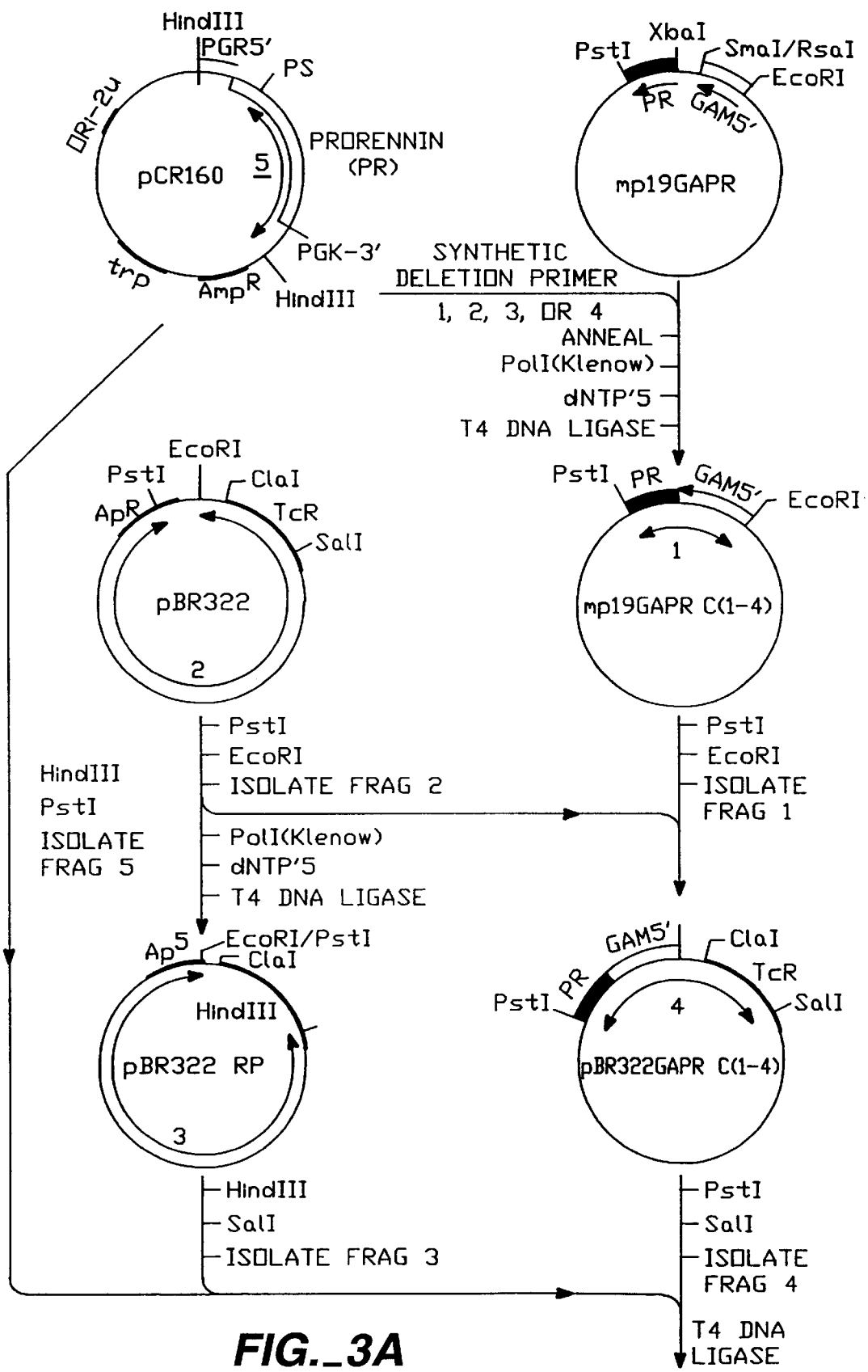
FIG._3A

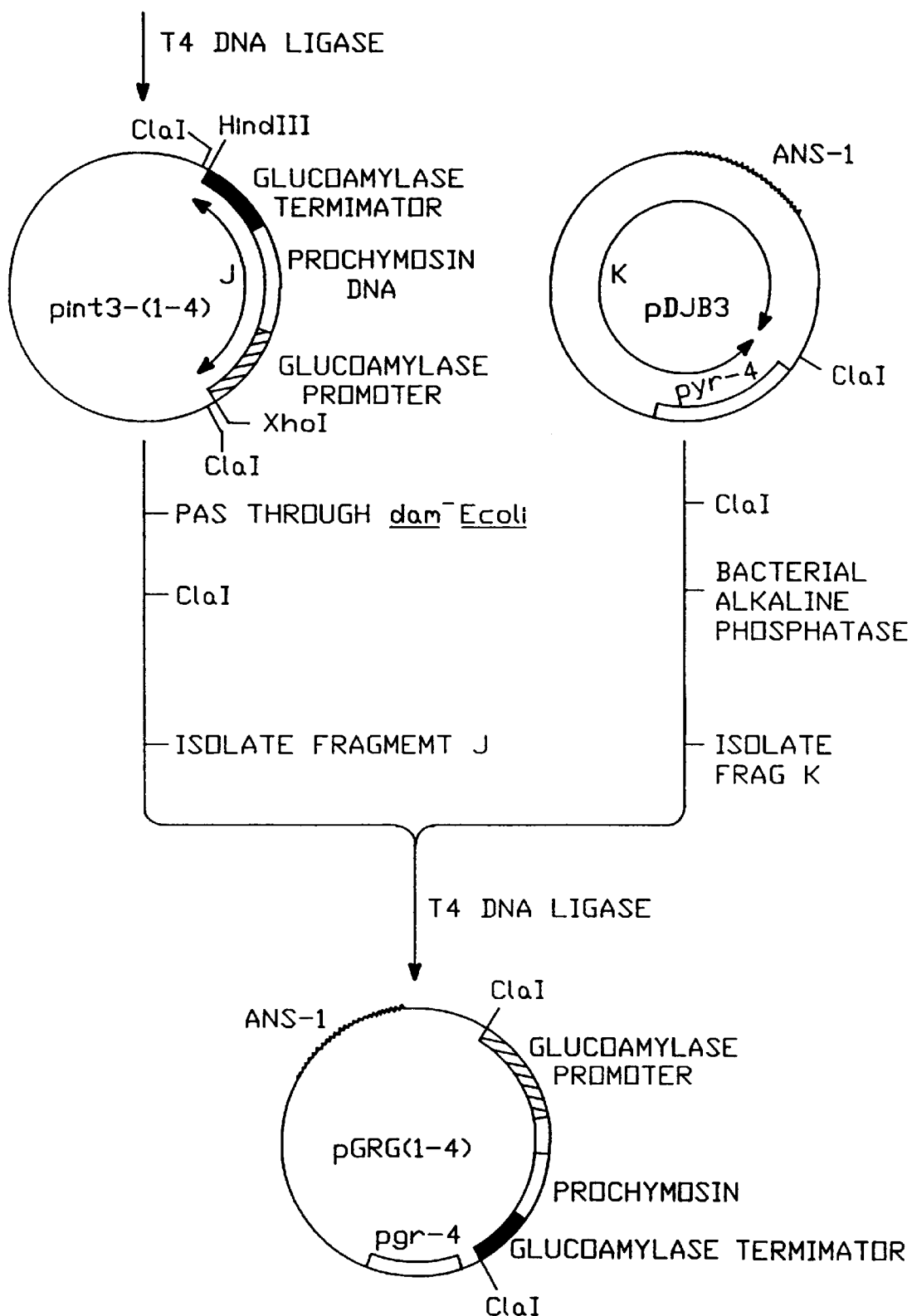
FIG._3B

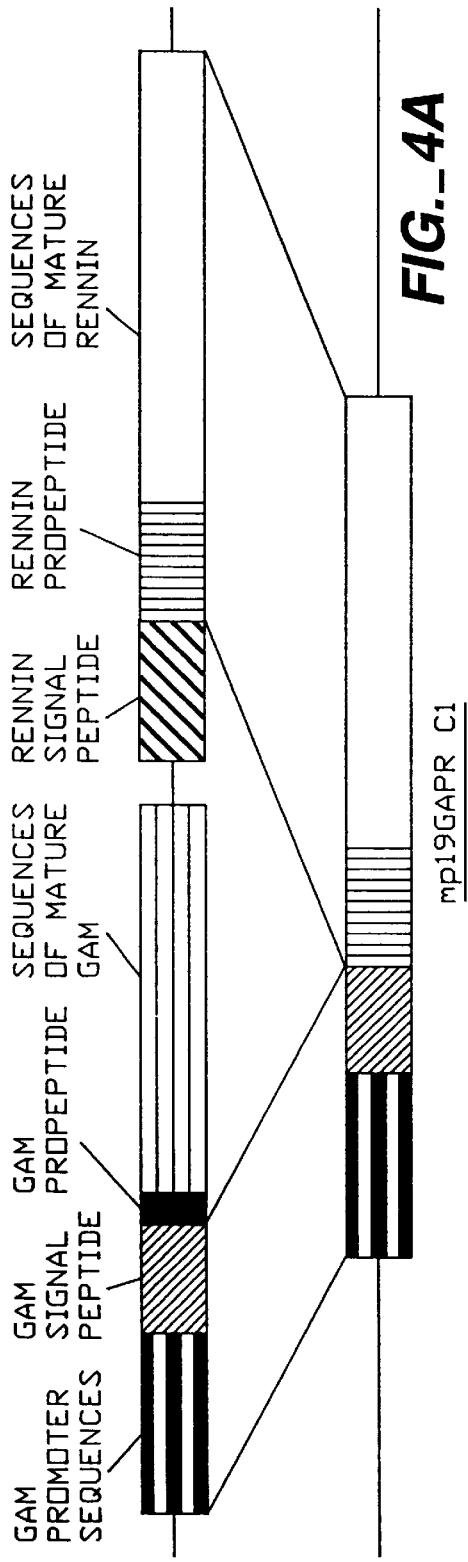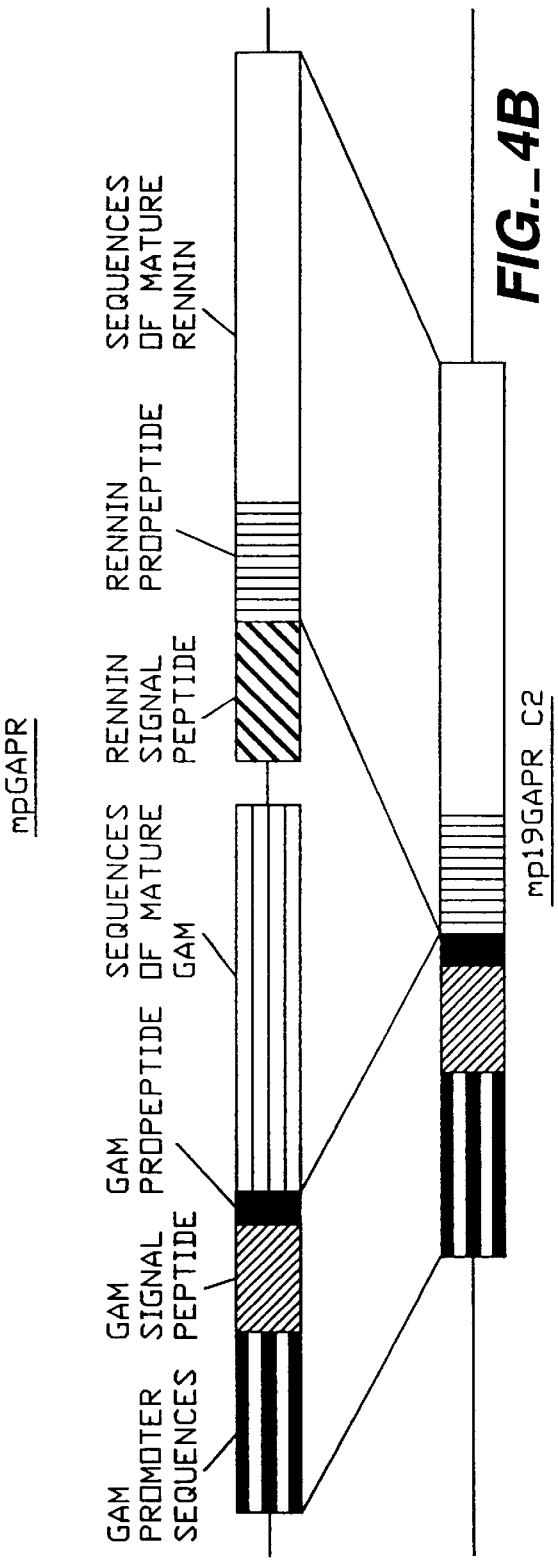
FIG._4A  FIG._4B

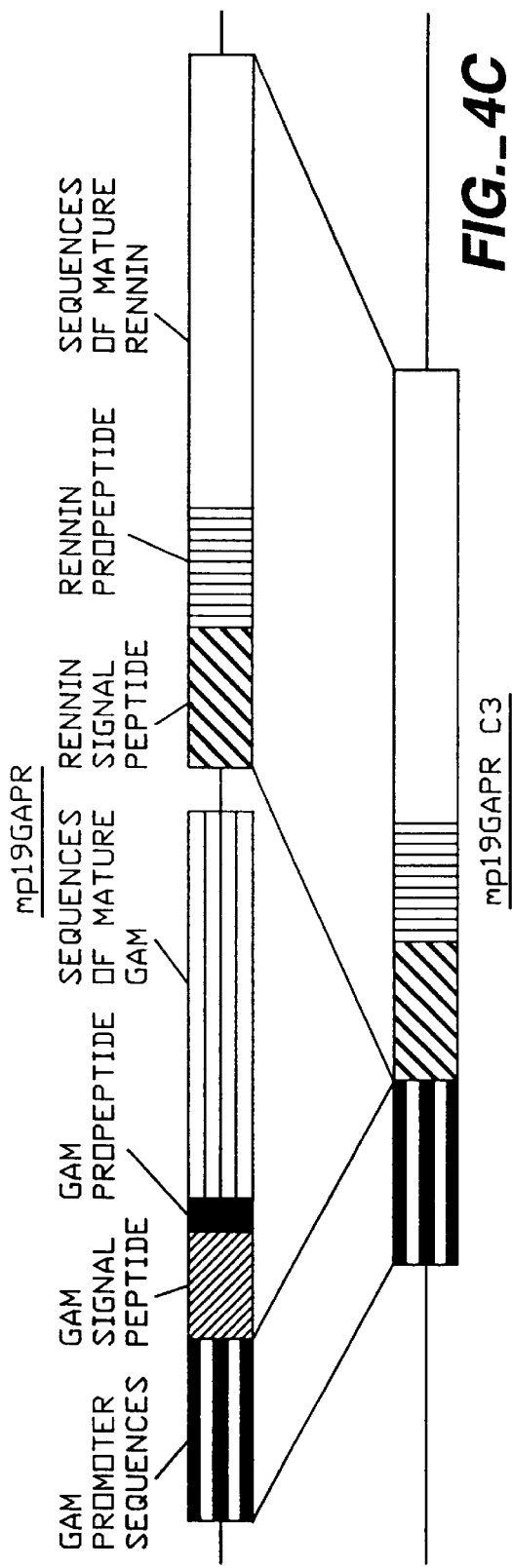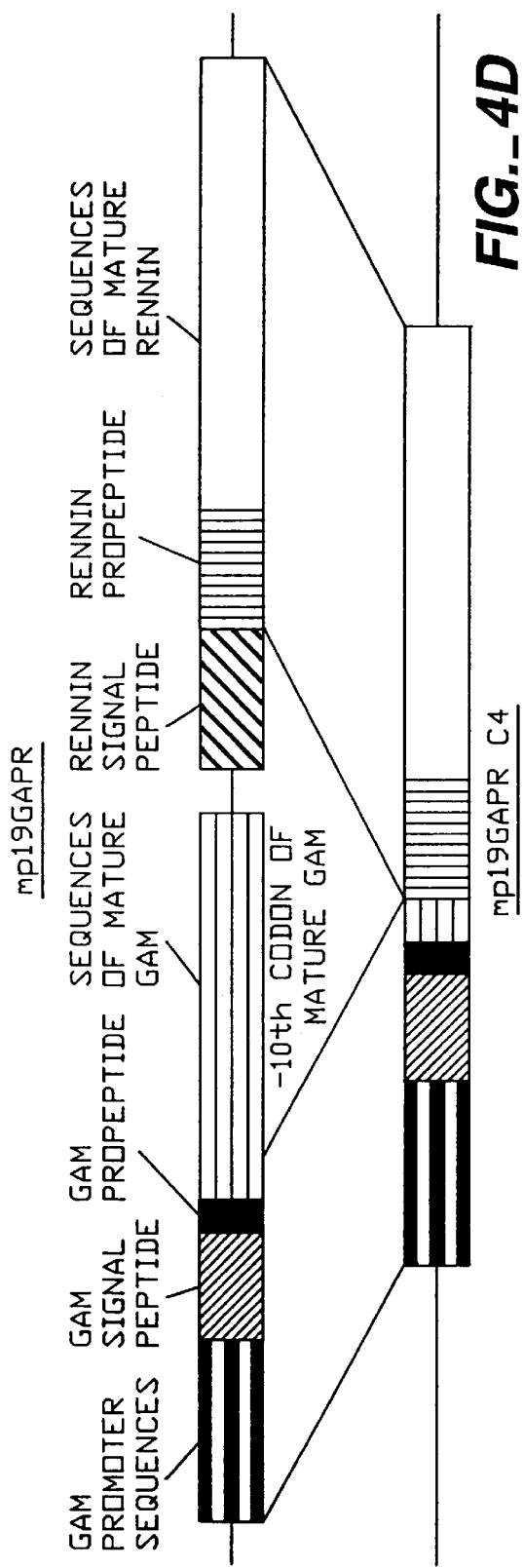

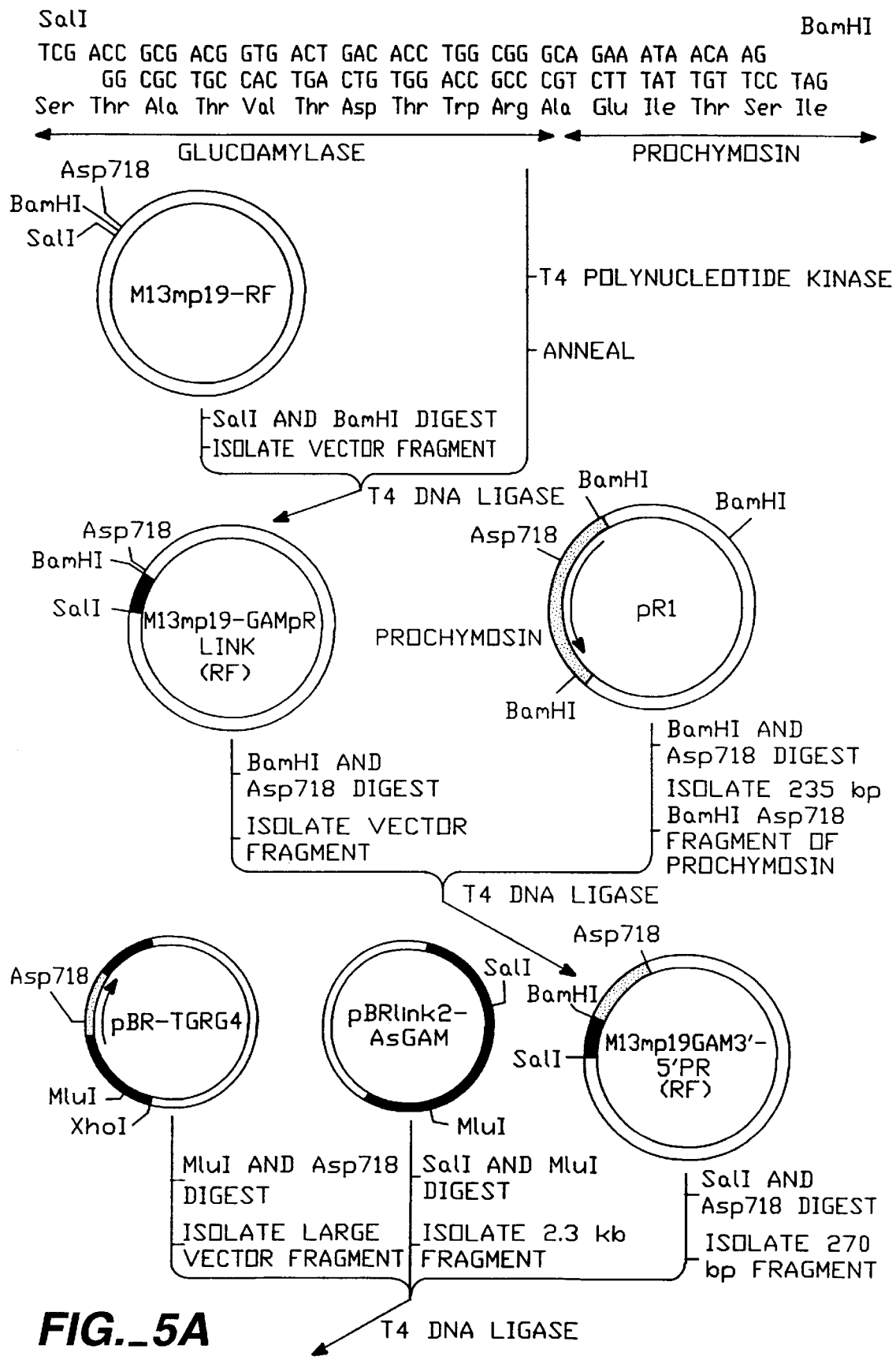
FIG._5A

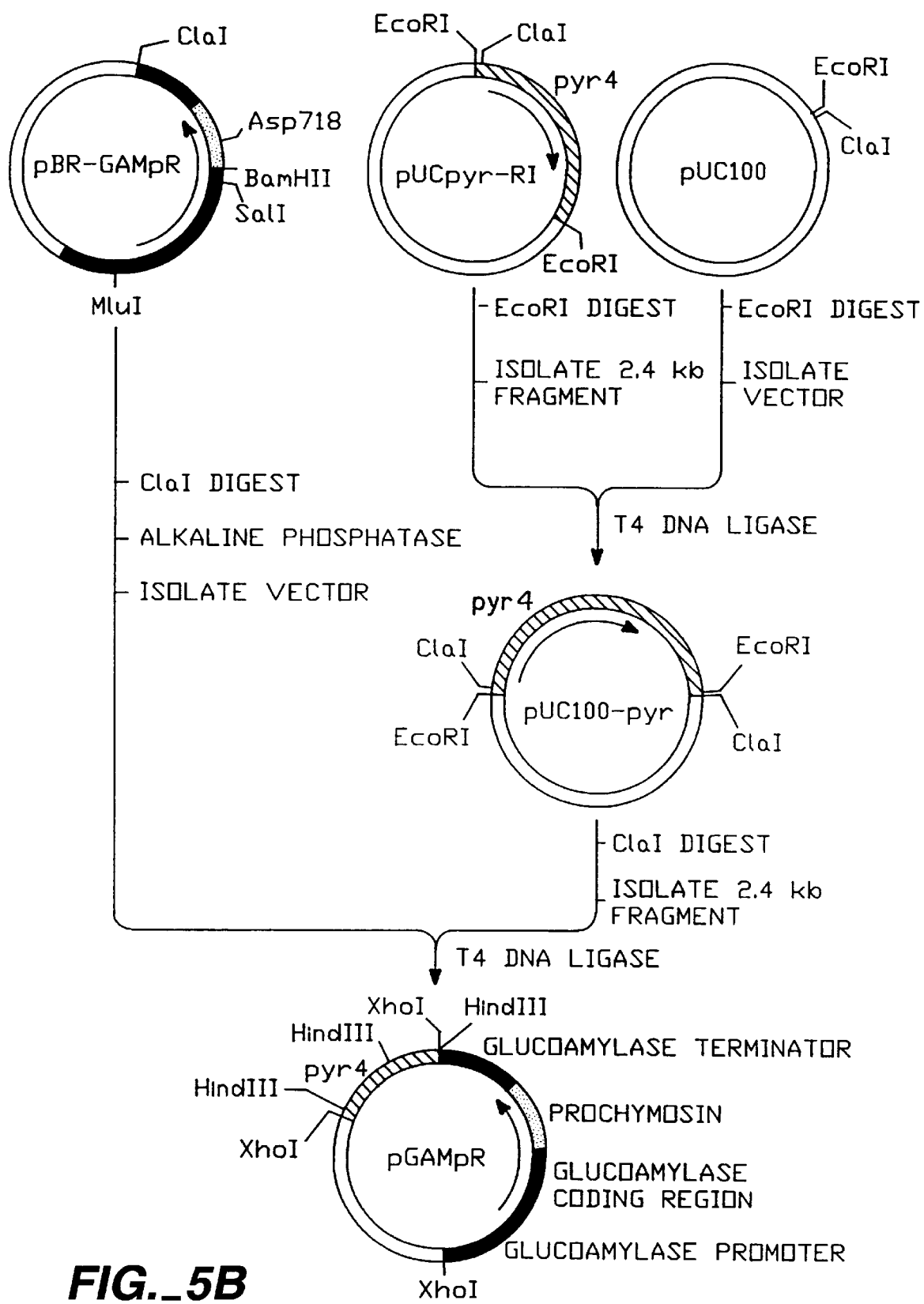
FIG._5B

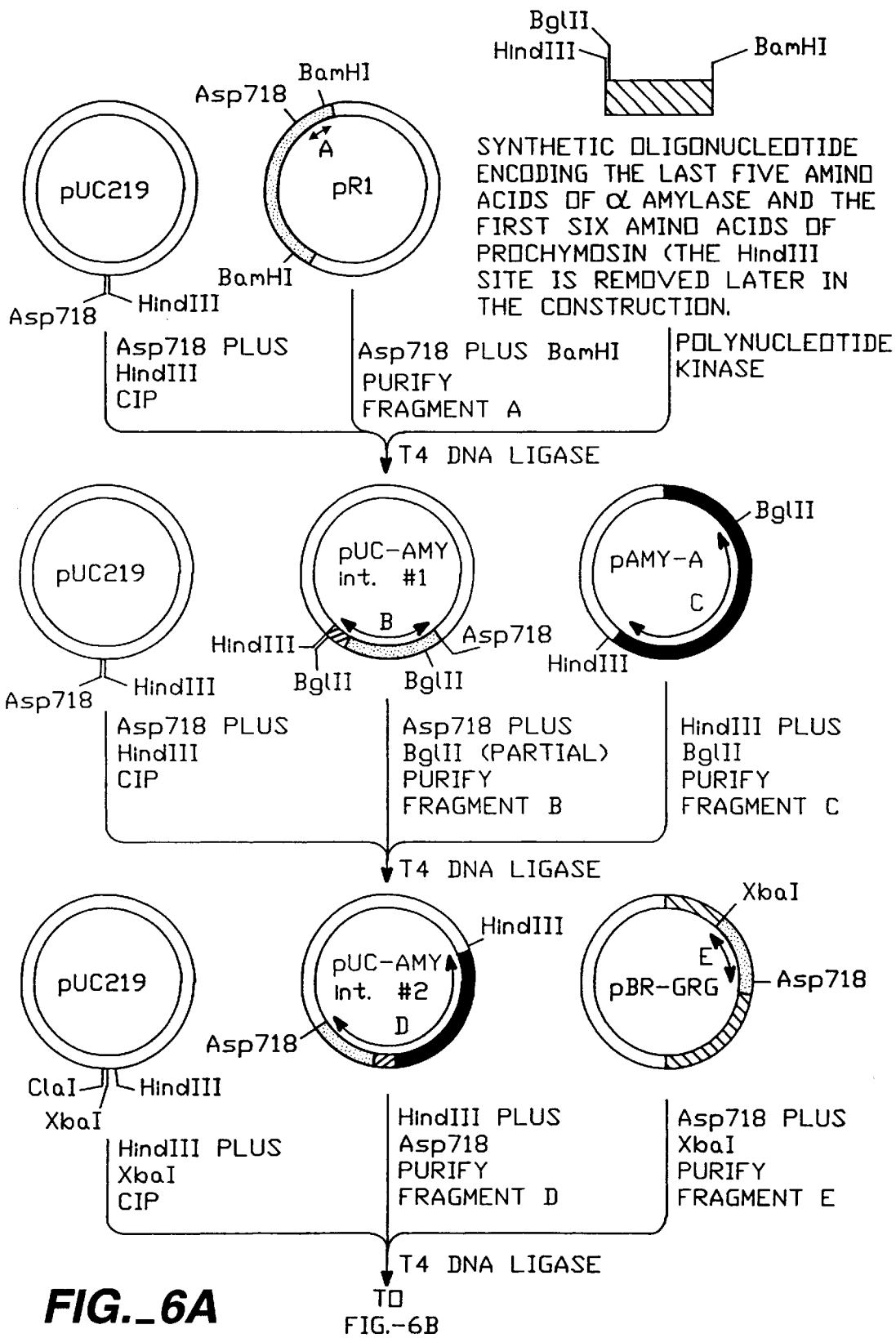
FIG._6A

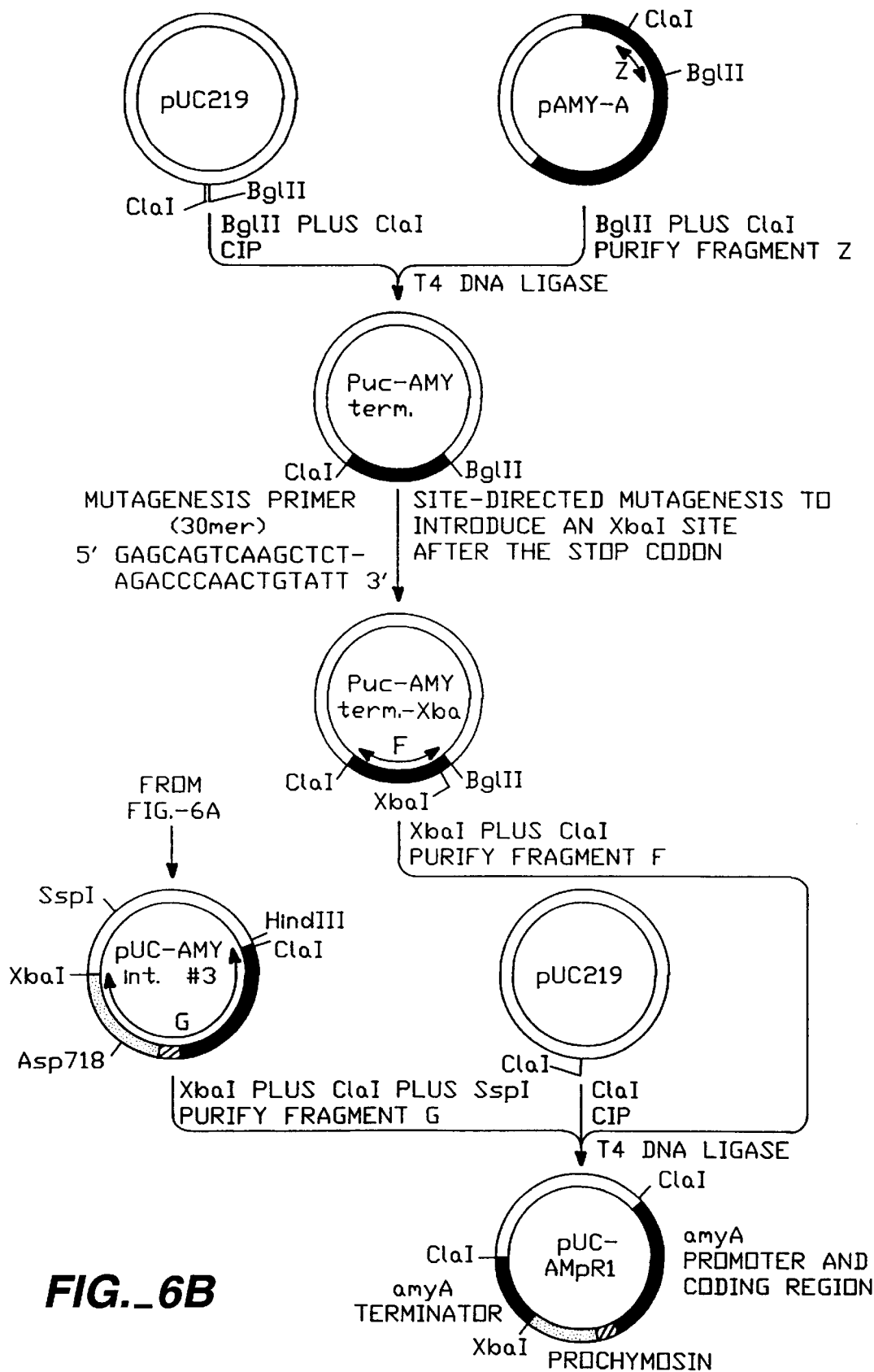
FIG._6B

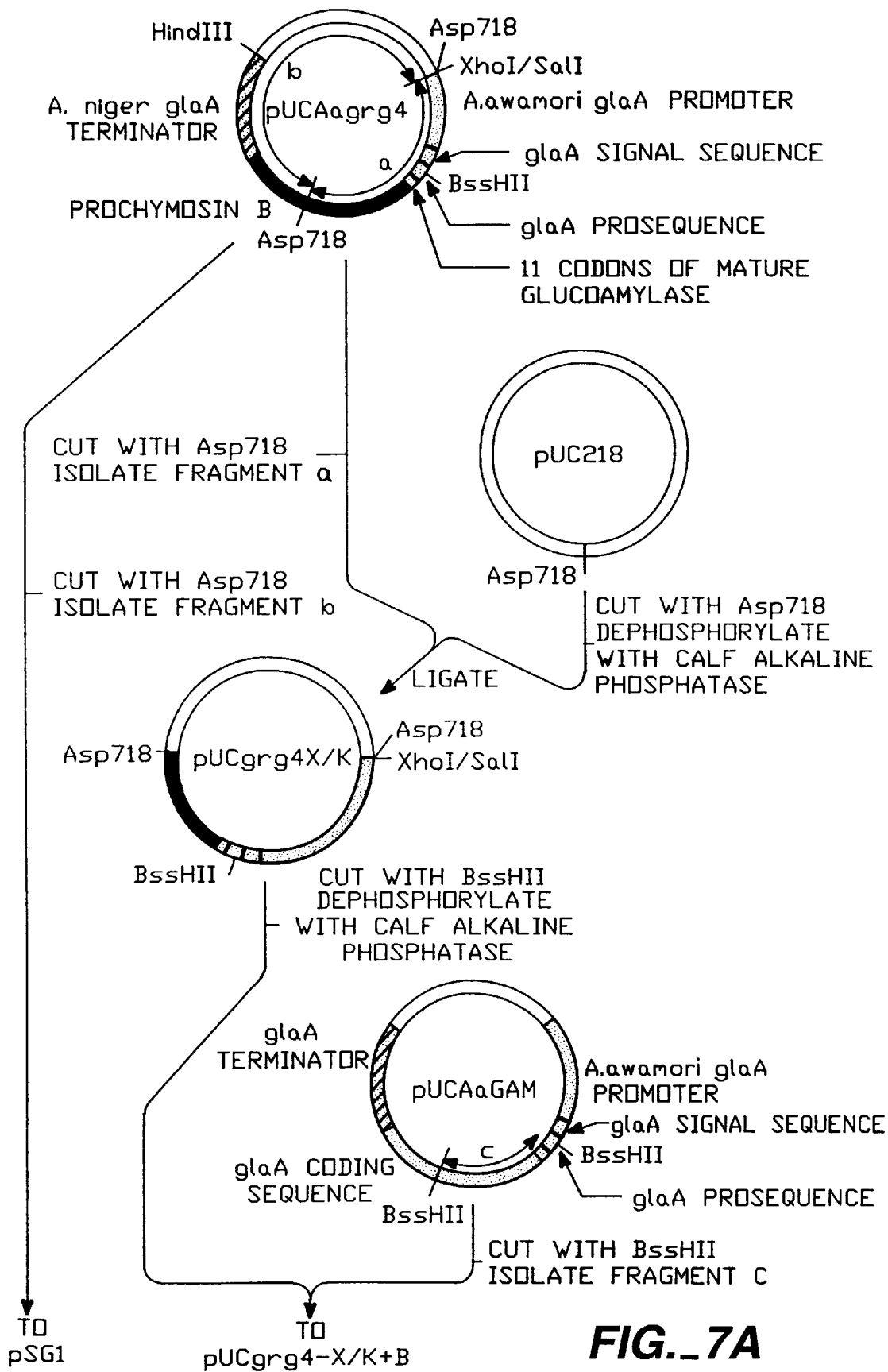
FIG._7A

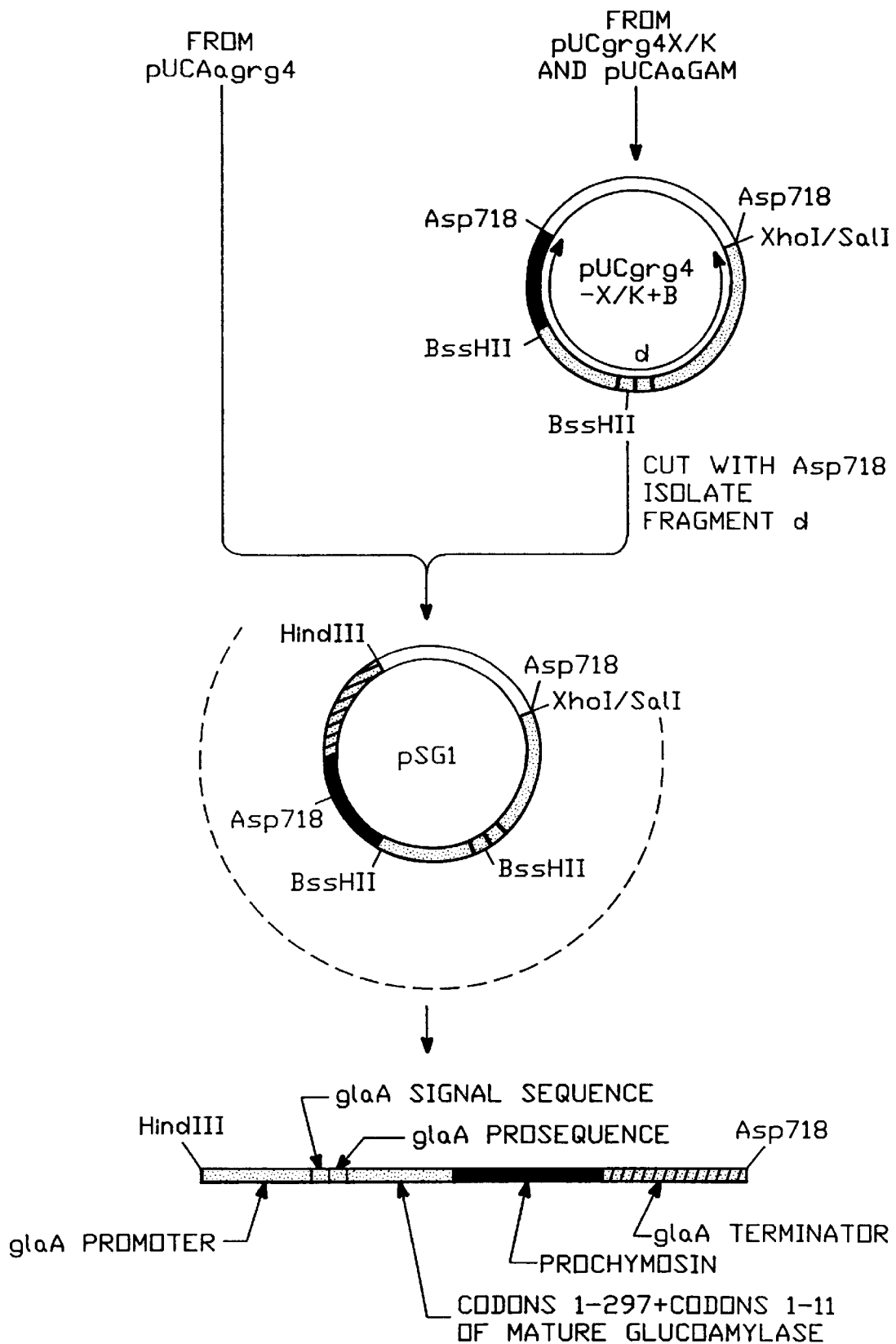
FIG._7B

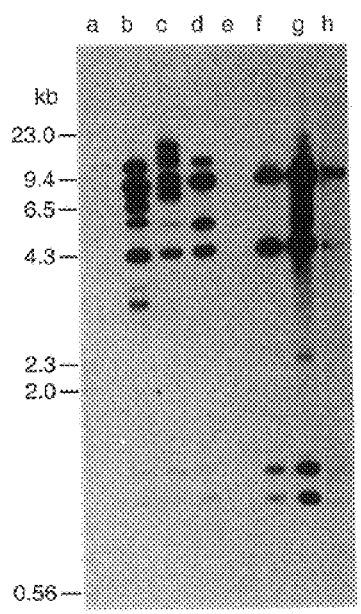
*FIG._8*
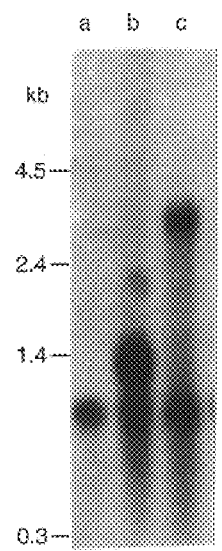
*FIG._9*
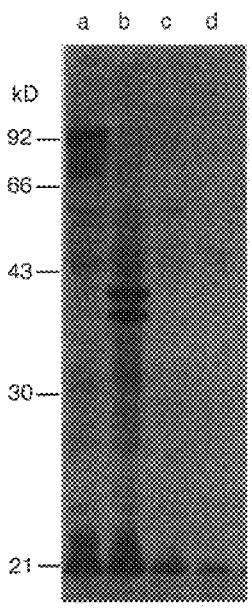
*FIG._10*

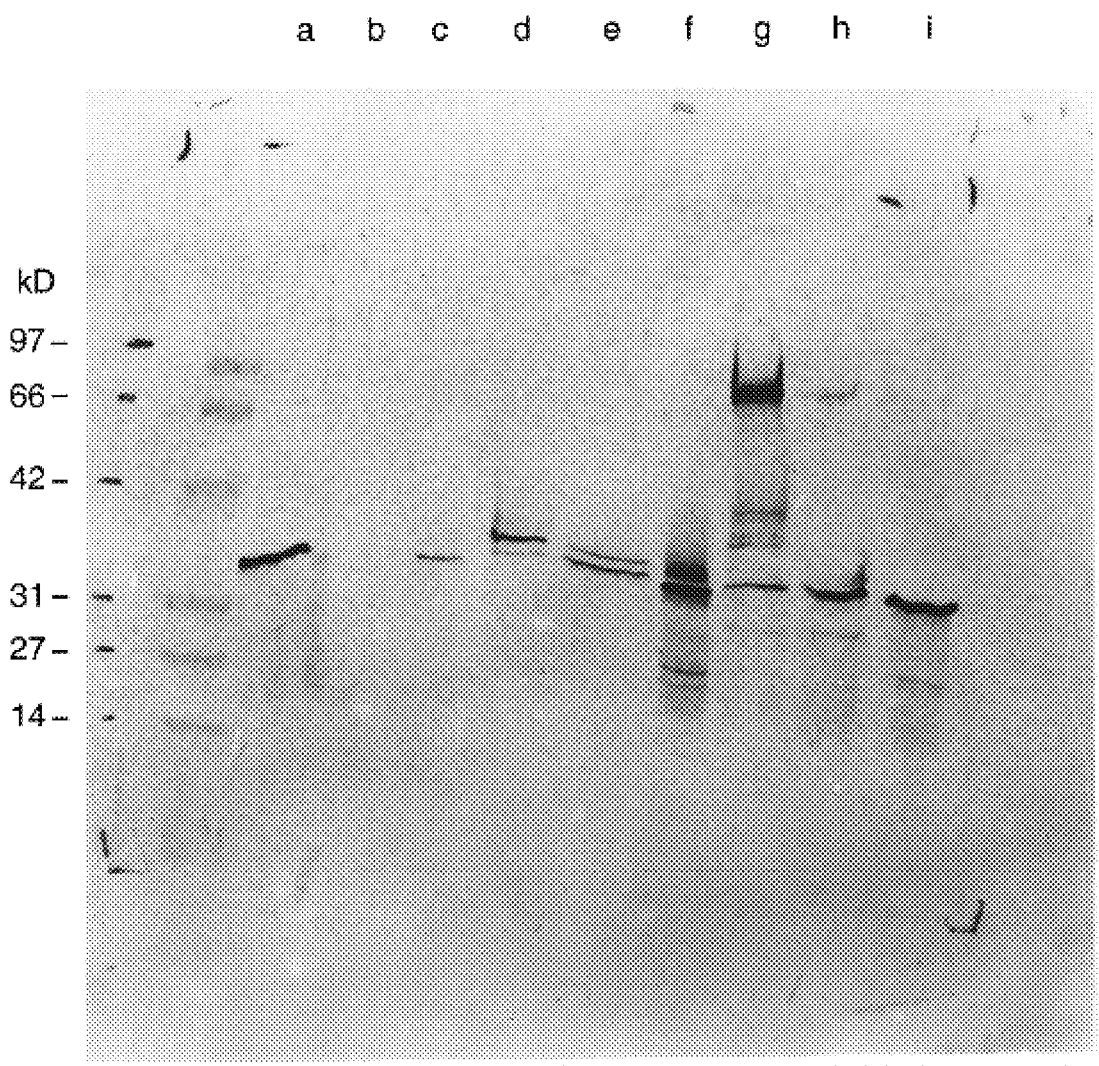
FIG._11

DNA SEQUENCES, VECTORS, AND FUSION POLYPEPTIDES TO INCREASE SECRETION OF DESIRED POLYPEPTIDES FROM FILAMENTOUS FUNGI

This is a continuation of application Ser. No 08/318,491 filed Oct. 5, 1994, now U.S. Pat. No. 5,679,543, which is a continuation of application Ser. No. 08/207,805 filed Mar. 7, 1994, now abandoned, which is a continuation of application Ser. No. 07/794,603, filed Nov. 15, 1991, now abandoned, which is a continuation of application Ser. No. 07/369,698, filed Jun. 16, 1989, now abandoned, which is a continuation-in-part of application Ser. No. 07/163,219, filed Feb. 26, 1988, now abandoned, which is a continuation of application Ser. No. 06/882,224, filed Jul. 7, 1986, now abandoned, which is a continuation-in-part of application Ser. No. 06/771,374, filed Aug. 29, 1985, now abandoned.

TECHNICAL FIELD OF THE INVENTION

The present invention is directed to increased secretion of desired polypeptides from filamentous fungi. The invention discloses DNA sequences, vectors, fusion polypeptides, and processes for obtaining enhanced production and secretion levels of the desired polypeptide. More particularly, the invention discloses DNA sequences, vectors, fusion polypeptides and processes for the increased secretion of bovine chymosin from filamentous fungi.

BACKGROUND OF THE INVENTION

One of the earlier successes of recombinant DNA technology involved the intracellular expression of the A and B chains of insulin in bacteria as carboxyl fusions to β-galactosidase. Goeddel, D. V. et al. (1979); *Proc. Natl. Acad. Sci. USA* 76, 106–110; Johnson, I. S. (1983) *Science* 219, 632–637. Since then, numerous examples have been described for the expression of fusion polypeptides comprising, in part, a heterologous polypeptide. Marston, F. A. O. (1986) *Biochem. J.* 240, 1–12 summarizes the production of heterologous polypeptides in *E.coli*. As described therein, a number of heterologous polypeptides have been expressed intracellularly as fusion polypeptide in *E. coli*. In addition, heterologous polypeptides have reportedly been secreted into the periplasmic space of such microbes by fusing the heterologous polypeptide with a signal sequence. In some cases, the heterologous polypeptide was secreted from *E. coli* into the culture medium when expressed with a signal sequence of bacterial origin. In those cases where a heterologous protein has been expressed as a fusion with the entire native protein of the host bacteria, the rational was primarily to increase stability or ease the purification of the fusion polypeptide.

For example, Scholtissek, S. et al. (1988) *Gene* 62 55–64, report the expression in *E. coli* of a triprotein consisting of bacterial β-galactosidase, a collagenase recognition site and the single stranded DNA binding protein from *E. coli*. The β-galactosidase portion of this fusion polypeptide reportedly was used to purify the fusion polypeptide from a crude cell lysate by affinity chromatography on APTG-Sepharose. The single stranded DNA binding protein from *E. coli* was thereafter isolated from the fusion polypeptide by reacting the collagenase recognition site with collagenase. Similarly, Smith, D. B. et al. (1988) *Gene* 67, 31–40 report the bacterial expression of a vector encoding a fusion polypeptide consisting of glutathione S-transferase fused at its C-terminus with a recognition site for blood coagulation factor $X_a$ which itself is fused to either of two heterologous polypeptides corresponding to different antigens of *P. falciparum*. In another example, Guan, C. et al. (1988) *Gene* 67, 21–30 report the expression and purification of fusion polypeptides consisting of maltose binding protein fused either to β-galactosidase or PstI Endonuclease, and a fusion protein consisting of the bacterial phoA signal, maltose binding protein and phoA protein. In the former cases, the fusion polypeptides were extracted from crude bacterial lysates by affinity chromatography on cross-linked amylose whereas, in the latter, the fusion protein was obtained from the periplasmic space after spheroplast formation and affinity chromatography on cross-linked amylose.

The expression of fusion polypeptides in yeast has also been reported. For example, Cousens, L. S. et al. (1987) *Gene* 61, 265–275, describe a fusion polypeptide consisting of a human superoxide dismutase-human proinsulin fusion protein with a methionine residue at the junction of the two proteins. Superoxide dismutase is an intracellular protein and the fusion polypeptide was reportedly expressed as an insoluble inclusion body within the yeast expression host with incorrect disulfide bonds. After sulfitollysis proinsulin was reportedly purified, renatured and processed to yield insulin after cleavage of the methionine residue with cyanogen bromide.

U.S. Pat. No. 4,751,180 to Cousens et al. states that a polypeptide of interest may be obtained in high yield from an expression host, such as yeast, when the polypeptide of interest is expressed as a completely heterologous fusion polypeptide. One of the heterologous polypeptides is produced in high yield in the expression host typically in amounts greater than five percent of the total protein produced by the host. The only high yield heterologous polypeptide disclosed, however, is that of the intracellular protein human superoxide dismutase which is fused to either proinsulin or IgF-2. The specification also states that a secretory leader and processing signal may be included as part of the fused polypeptide. No example is provided which indicates that secretion would be obtained and, if obtained, would be at levels higher than that which have been obtained using a fusion construction which detected the high yield heterologous protein in a fusion consisting of a secretory leader sequence fused to only the polypeptide of interest, e.g. proinsulin or insulin-like growth factor (IgF-2).

Heterologous gene expression has also been reported in filamentous fungi. For example, Christensen, T. et al. (1988) *Bio/Technology* 6, 1419–1422 have reported an expression vector utilizing the α-amylase promotor from *A. oryzae* to express the prepro form of aspartyl proteinase from the filamentous fungus *Rhizomuchor miehei*. When expressed in *A. oryzae,* aspartyl proteinase was obtained from the culture medium. When Gwynne, D. I. et al. (1987) *Bio/Technology* 5, 713–719, report the expression and secretion of human interferon and bacterial endoglucanase from filamentous fungi by expressing these genes with either a fungal glucoamylase signal or a synthetic consensus signal sequence.

Upshall, A. et al. (1987) *Bio/Technology* 5, 1301–1304 report the expression and secretion of human tissue plasminogen activator by expressing the gene encoding the preform of t-PA in a filamentous fungus. Further, Turnbull, I. F. et al. (1989) *Bio/Technology* 7, 169–174 report an attempt to express and secrete bacterial enterotoxin subunit B from filamentous fungi. No secreted material, however, was detected.

Bovine prochymosin has reportedly been expressed in *Escherichia coli,* the yeasts *Saccharomyces cerevisiae* and *Yarrowia lipolytica,* and in filamentous fungi by the inventor in Asperaillus species. In *E. coli* prochymosin, with the first four amino acid residues replaced by an amino-terminal fragment of the trpE gene, has reportedly been produced under the control of the trp promoter (Nishimori, K. et al. (1984) *Gene* 29, 41–49). The fusion protein accumulated as inclusion bodies in the cytoplasm but after appropriate extraction conditions could be activated to yield mature chymosin.

Moir et al. (1985) (*In: Developments in Industrial Microbiology*. Vol. 26. Underkofler, L. A. (ed.). Society for Industrial Microbiology, Arlington, Va., U.S.A.) described intracellular production of prochymosin in *S. cerevisiae*. The protein was synthesized with various segments of phosphoglycerate kinase, triosephosphate isomerase or galactokinase attached to the amino terminus, allowing increased production compared to direct expression from the same promoters. It was suggested that the increase in production was due to more efficient translation of the mRNA. Moir et al. also reported secretion of prochymosin from *S. cerevisiae*, in the form of a fusion with the first few residues of invertase or alpha factor. The extracellular prochymosin was activated at low pH to give mature chymosin despite the additional amino acids on the prosequence. Similarly, activatable prochymosin was secreted from the yeast *Y. lipolytica* with either 14 or 90 residues of native alkaline extracellular protease attached to the amino terminus (Franke, A. E. et al. (1988) *In: Developments in Industrial Microbiology*. Vol. 29. Pierce, G. (ed.). Society for Industrial Microbiology, Arlington, Va., U.S.A.). In this report, no more than about 20% of the amino terminus of the protease was used to generate the fusion polypeptides and no apparent advantage accrued from expression as fusion polypeptides. Active calf chymosin has also been produced in the filamentous fungus *Trichoderma reesei* (Harkki, A. et al. (1989) Bio/Technology 7, 596–603. The cellobiohydrolase I gene (cbhI) promoter and terminator regions were employed and four different constructions were made employing different signal sequences fused to prochymosin cDNA. Either the chymosin signal sequence, cbhI signal sequence, a hybrid cbhI/chymosin signal sequence or the cbhI signal sequence plus 20 amino acids of mature cbhI were fused to the amino terminus of prochymosin. Slightly better production was obtained from the latter construction although insufficient numbers of transformants were examined to confirm this. Secretion was inefficient with approximately 66% of the chymosin-derived material remaining within the cell of transformants regardless of the type of vector construction used.

The glaA gene encodes glucoamylase which is highly expressed in many strains of *Aspergillus niger* and *Aspergillus awamori*. The promoter and secretion signal sequence of the glaA gene have been used to express heterologous genes in Aspergilli including bovine chymosin in *Aspergillus nidulans* and *A. awamori* as previously described by the inventors (Cullen, D. et al. (1987) *Bio/Technology* 5, 713–719) and EPO Publication No. 0 215 594). In the latter experiments, a variety of constructs were made, incorporating prochymosin cDNA, either the glucoamylase or the chymosin secretion signal and, in one case, the first 11 codons of mature glucoamylase. Maximum yields of secreted chymosin obtained from *A. awamori* were below 15 mg/l in 50 ml shake flask cultures and were obtained using the chymosin signal sequence encoded by pGRG3. These previous studies indicated that integrated plasmid copy number did not correlate with chymosin yields, abundant polyadenylated chymosin mRNA was produced, and intracellular levels of chymosin were high in some transformants regardless of the source of secretion signal. It was inferred that transcription was not a limiting factor in chymosin production but that secretion may have been inefficient. It was also evident that the addition of a small amino terminal segment (11 amino acids) of glucoamylase to the propeptide of prochymosin did not prevent activation to mature chymosin. The amount of extracellular chymosin obtained with the first eleven codons of glucoamylase, however, was substantially less than that obtained when the glucoamylase signal was used alone.

Accordingly, an object of the invention herein is to provide for the expression and enhanced secretion of desired polypeptides by and from filamentous fungi including fusion DNA sequences, expression vectors containing such DNA sequences, transformed filamentous fungi, fusion polypeptides and processes for expressing and secreting high levels of such desired polypeptides.

It is a further object of the invention to provide for the expression and enhanced secretion of chymosin from filamentous fungi including fusion DNA sequences, vectors containing such DNA sequences transformed filamentous fungi, fusion chymosin polypeptides and processes for expressing and secreting high levels for chymosin.

The references discussed above are provided solely for their disclosure prior to the filing date of the instant case. Nothing herein is to be construed as an admission that the inventors are not entitled to antedate such disclosure by virtue of prior invention or priority based on earlier filed applications.

SUMMARY OF THE INVENTION

In accordance with the above objects, the invention includes novel fusion DNA sequences encoding fusion polypeptides which when expressed in a filamentous fungus result in the expression of fusion polypeptides which when secreted result in increased levels of secretion of the desired polypeptide as compared to the expression and secretion of such polypeptides from filamentous fungi transformed with previously used DNA sequences.

The fusion DNA sequences comprise from the 5' terminus four DNA sequences which encode a fusion polypeptide comprising, from the amino to carbonyl-terminus, first, second, third and fourth amino acid sequences. The first DNA sequence encodes a signal peptide functional as a secretory sequence in a first filamentous fungus. The second DNA sequence encodes a secreted polypeptide or portion thereof which is normally secreted from the same filamentous fungus or a second filamentous fungus. The third DNA sequence encodes a cleavable linker polypeptide while the fourth DNA sequence encodes a desired polypeptide. When the fusion DNA sequence is expressed either in the first or second filamentous fungus, increased secretion of the desired polypeptide is obtained as compared to that which is obtained when the desired polypeptide is expressed from DNA sequences encoding a fusion polypeptide which does not contain the second polypeptide normally secreted from either of the filamentous fungi.

The invention also includes expression vectors containing the above fusion DNA sequence and filamentous fungi transformed with such expression vectors. The invention also includes the fusion polypeptide encoded by such fusion DNA sequences.

Further, the invention includes a process for producing a desired polypeptide comprising transforming a host filamentous fungus with the above described expression vector and culturing the host filamentous fungus to secrete the desired polypeptide into the culture medium.

BRIEF DESCRIPTION OF THE DRAWINGS

FIG. 1 depicts the construction of pBRΔgam-arg.

FIG. 2 depicts the disruption of the glaA gene by replacement of the 5.5 kb DNA chromosomal fragment with a 4.5 kb fragment from pBRΔgam-argB.

FIGS. 3A and 3B depict the construction of pGRG(1–4).

FIGS. 4A, 4B, 4C and 4D depict the various cassette inserts used to generate pGRG1 through pGRG4.

FIGS. 5A and 5B depict the construction of pGAMpR.

FIG. 6 depicts the construction of pUCAMpR1.

FIG. 7 depicts the construction of pSG1.

FIG. 8 depicts Southern blot analysis of DNA from transformants of strains GC12 and GCΔGAMpR.

FIG. 9 depicts Northern blot analysis of RNA from strain GC12 and transformants 12grg1–1a and 12gampr4.

FIG. 10 depicts products of in vitro translation of RNA from strain GC12 and transformants 12grg1–1a and 12gampr4.

FIG. 11 depicts Western analysis of chymosin in culture supernatants of transformants 12grg1–1a and 12gampr4.

DETAILED DESCRIPTION

The inventors have discovered that desired polypeptides can be expressed and secreted at levels higher than that previously obtained by fusing the desired polypeptide with a polypeptide which is normally secreted from a filamentous fungus. Previously, the inventors discovered that heterologous polypeptides such as bovine chymosin and glucoamylase and carboxyl (=aspartyl) protease from filamentous fungi could be expressed and secreted from Aspergillus species as described in the parent applications and EPO Publication No. 0 215 594, each of which are expressly incorporated herein by reference.

For example, the inventors previously achieved expression and secretion of bovine chymosin from *Aspergillus nidulans* at levels approaching 1.5 micrograms per ml of medium when expressed as a fusion between the glucoamylase signal peptide and the pro-form of chymosin. The vector encoding this particular construction is designated pGRG1 (see FIGS. 3 and 4A). However, when the glucoamylase signal peptide together with the glucoamylase propeptide and the first eleven amino acids of glucoamylase were fused to prochymosin, secretion levels were substantially reduced to about half of the term obtained in the previous construction, i.e. reduced to approximately 0.75 μg per ml of medium. This vector was previously identified as pGRG4 and is identified in FIGS. 3 and 4D. All of the plasmids pGRG1, pGRG3 and pGRG4 (see FIGS. 3 and 4A, B, C and D) have been transformed into *A. awamori*. The transformant which produced the greatest amount of extracellular chymosin was obtained using pGRG3. With improvements to culture medium and conditions the highest level of secreted chymosin obtained was below 15 μg/mL as measured by enzyme immunoassay (which will detect inactive and degraged chymosin in addition to mature chymosin).

By using the fusion DNA constructions described herein, a dramatic increase in extracellular chymosin has been obtained. In some cases chymosin levels are approximately 20 fold in excess of that obtained previously. Commensurate with this increase in secretion is the reduction in the amount of chymosin maintained intracellularly in the filamentous fungi expression host. Well over 50% and, in some cases, as much as almost 98% of the chymosin produced previously was maintained intracellularly (see Table II). When the vectors encoding the DNA sequences of the invention herein were used, however, thirty percent or less, and in some cases, less than 1% of the chymosin expressed was maintained intracellularly.

The increased secretion levels of chymosin are the result of expressing chymosin in its pro-form as a fusion polypeptide with a polypeptide normally secreted by a filamentous fungus. In the preferred embodiments, glucoamylase from *A. awamori* encoded by the glaA gene, including the secretory signal sequence of glucoamylase is fused to the amino-terminus of prochymosin. The presence of the glucoamylase signal sequence and mature glucoamylase peptide sequences facilitate the enhanced secretion of the fusion polypeptide into the culture medium. Mature chymosin is then obtained by acidifying the medium to process the chymosin prosequence to produce active chymosin by removal of the propeptide.

As used herein, a "fusion DNA sequence" comprises from 5' to 3' first, second, third and fourth DNA sequences. The "first DNA sequence" encodes a signal peptide functional as a secretory sequence in a first filamentous fungus. Such signal sequences include those from glucoamylase, α-amylase and aspartyl proteases from *Aspergillus awamori, Aspergillus niger, Aspergillus oryzae,* signal sequences from cellobiohydrolase I, cellobiohydrolase II, endoglucanase I, endoglucanase III from Trichoderma, signal sequences from glucoamylase from Neurospora and Humicola as well as signal sequences from eukaryotes including the signal sequence from bovine chymosin, human tissue plasminogen activator, human interferon and synthetic consensus eukaryotic signal sequences such as that described by Gwynne (1987) supra. Particularly preferred signal sequences are those derived from polypeptides secreted by the expression host used to express and secrete the fusion polypeptide. For example, the signal sequence from glucoamylase from *Asperaillus awamori* is preferred when expressing and secreting a fusion polypeptide from *Aspergillus awamori*. As used herein, first amino acid sequences correspond to secretory sequences which are functional in a filamentous fungus. Such amino acid sequences are encoded by first DNA sequences as defined.

As used herein, "second DNA sequences" encode "secreted polypeptides" normally expressed from filamentous fungi. Such secreted polypeptides include glucoamylase, α-amylase and aspartyl proteases from *Aspergillus awamori, Aspergillus niger,* and *Aspergillus oryzae,* cellobiohydrolase I, cellobiohydrolase II, endoglucanase I and endoglucanase III from Trichoderma and glucoamylase from Neurospora species and Humicola species. As with the first DNA sequences, preferred secreted polypeptides are those which are naturally secreted by the filamentous fungal expression host. Thus, for example when using *Aspergillus awamori,* preferred secreted polypeptides are glucoamylase and α-amylase from *Aspergillus awamori,* most preferably glucoamylase.

As used herein, "third DNA sequences" comprise DNA sequences encoding a cleavable linker polypeptide. Such sequences include those which encode the prosequence of bovine chymosin, the prosequence of subtilisin, prosequences of retrovirul proteases including human immunodeficiency virus protease and DNA sequences encoding amino acid sequences recognized and cleaved by trypsin, factor $X_a$ collagenase, clostripin, subtilisin, chymosin, yeast KEX2 protease and the like. See e.g. Marston, F. A. O. (1986) *Biol. Chem J.* 240, 1–12. Such third DNA sequences may also encode the amino acid methionine which may be selectively cleaved by cyanogen bromide. It should be understood that the third DNA sequence need only encode that amino acid sequence which is necessary to be recognized by a particular enzyme or chemical agent to bring about cleavage of the fusion polypeptide. Thus, the entire prosequence of, for example, chymosin or subtilisin need not be used. Rather, only that portion of the prosequence which is necessary for recognition and cleavage by the appropriate enzyme is required.

As used herein, "fourth DNA sequences" encode "desired polypeptides." Such desired polypeptides include mammalian enzymes such as bovine chymosin, human tissue plasminogen activator etc., mammalian hormones such as human growth hormone, human interferon, human interleukin and mammalian proteins such as human serum albumin. Desired polypeptides also induce bacterial enzymes such as α-amylase from Bacillus species, lipase from Pseudomonas species, etc. Desired polypeptides further include fungal enzymes such as lignin peroxidase and $Mn^{2+}$-dependent peroxidase from Phanerochaete, glucoamylase from Humicola species and aspartyl proteases from Mucor species.

The above-defined four DNA sequences encoding the corresponding four amino acid sequences are combined to form a "fusion DNA sequence." Such fusion DNA sequences are assembled in proper reading frame from the 5' terminus to 3' terminus in the order of first, second, third and fourth DNA sequences. As so assembled, the DNA sequence will encode a "fusion polypeptide" encoding from its aminoterminus a signal peptide functional as a secretory sequence in a filamentous fungus, a secreted polypeptide or portion thereof normally secreted from a filamentous fungus, a cleavable linker polypeptide and a desired polypeptide.

As indicated, the first DNA sequence encodes a signal peptide functional as a secretory signal in a first filamentous fungus. The signal sequences may be derived from a secreted polypeptide from a particular species of filamentous fungus. As also indicated, the second DNA sequence encodes a second amino acid sequence corresponding to all or part of a polypeptide normally secreted by either the first filamentous fungus (from which the signal peptide is obtained) or a second filamentous fungus (if the signal peptide and secreted polypeptide are from different filamentous fungi or if the signal peptide is obtained from a source other than a filamentous fungus, e.g. the chymosin signal from bovine species).

As indicated, all or part of the mature sequence of the secreted polypeptide is used in the construction of the fusion DNA sequences. It is preferred that full length secreted polypeptides be used to practice the invention. However, functional portions of the secreted polypeptide may be employed. As used herein a "portion" of a secreted polypeptide is defined functionally as that portion of a secreted polypeptide which when combined with the other components of the fusion polypeptide defined herein results in increased secretion of the desired polypeptide as compared to the level of desired polypeptide secreted when an expression vector is used which does not utilize the secreted polypeptide. Thus, the secretion level of a fusion DNA sequence encoding first, second, third and fourth amino acid sequences (the second DNA sequence containing all or a portion of a secreted polypeptide) is compared to the secretion level for a second fusion polypeptide containing only first, third and fourth amino acid sequences (i.e., without a secreted polypeptide or a portion thereof). Those amino acid sequences from the secreted polypeptide, and DNA sequences encoding such amino acids, which are capable of producing increased secretion as compared to the second fusion polypeptide comprise the "portion" of the secreted polypeptide as defined herein.

Generally, such portions of the secreted polypeptide comprise greater than 50% of the secreted polypeptide, preferably greater than 75%, most preferably greater than 90% of the secreted polypeptide. Such portions comprise preferably the amino-terminal portion of the secreted polypeptide.

The "filamentous fungi" of the present invention are eukaryotic microorganisms and include all filamentous forms of the subdivision Eumycotina, Alexopoulos, C. J. (1962), *Introductory Mycology*, New York: Wiley. These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligately aerobic. In contrast, vegetative growth by yeasts such as *S. cerevisiae* is by budding of a unicellular thallus, and carbon catabolism may be fermentative. *S. cerevisiae* has a prominent, very stable diploid phase whereas, diploids exist only briefly prior to meiosis in filamentous fungi like Aspergilli and Neurospora. *S. cervisiae* has 17 chromosomes as opposed to 8 and 7 for *A. nidulans* and *N. crassa* respectively. Recent illustrations of differences between *S. cerevisiae* and filamentous fungi include the inability of *S. cerevisiae* to process Aspergillus and Trichoderma introns and the inability to recognize many transcriptional regulators of filamentous fungi (Innis, M. A. et al. (1985) *Science*, 228, 21–26).

Various species of filamentous fungi may be used as expression hosts including the following genera: Aspergillus, Trichoderma, Neurospora, Penicillium, Cephalosporium, Achlya, Podospora, Endothia, Mucor, Cochliobolus and Pyricularia. Specific expression hosts include *A. nidulans,* (Yelton, M., et al. (1984) *Proc. Natl. Acad. Sci. USA*, 81, 1470–1474; Mullaney, E. J. et al. (1985) *Mol. Gen. Genet.* 199, 37–45; John, M. A. and J. F. Peberdy (1984) *Enzyme Microb. Technol.* 6, 386–389; Tilburn, et al. (1982) *Gene* 26, 205–221; Ballance, D. J. et al., (1983) *Biochem. Biophys. Res. Comm.* 112, 284–289; Johnston, I. L. et al. (1985) *EMBO J.* 4, 1307–1311) *A. niger,* (Kelly, J. M. and M. Hynes (1985) *EMBO* 4, 475–479) *A. awamori,* e.g., NRRL 3112, ATCC 22342, ATCC 44733, ATCC 14331 and strain UVK 143f, *A. oryzae,* e.g., ATCC 11490, *N. crassa* (Case, M. E. et al. (1979) *Proc. Natl. Acad. Scie. USA* 76, 5259–5263; Lambowitz U.S. Pat. No. 4,486,553; Kinsey, J. A. and J. A. Rambosek (1984) *Molecular and Cellular Biology* 4, 117–122; Bull, J. H. and J. C. Wooton (1984) *Nature* 310, 701–704), *Trichoderma reesei,* e.g. NRRL 15709, ATCC 13631, 56764, 56765, 56466, 56767, and *Trichoderma viride,* e.g., ATCC 32098 and 32086. A preferred expression host is *A. awamori* in which the gene encoding the major secreted aspartyl protease has been deleted. The production of this preferred expression host is described in U.S. patent application Ser. No. 214,237 filed Jul. 1, 1988, now abandoned, expressly incorporated herein by reference.

As used herein, a "promotor sequence" is a DNA sequence which is recognized by the particular filamentous fungus for expression purposes. It is operably linked to a DNA sequence encoding the above defined fusion polypeptide. Such linkage comprises positioning of the promoter with respect to the translation initiation codon of the DNA sequence encoding the fusion DNA sequence. The promoter sequence contains transcription and translation control sequences which mediate the expression of the fusion DNA sequence. Examples include the promoter from the *A. awamori* or *A. niger* glucoamylase genes (Nunberg, J. H. et al. (1984) *Mol. Cell. Biol.* 4, 2306–2315; Boel, E. et al. (1984) *EMBO J.* 3, 1581–1585), the *Mucor miehei* carboxyl protease gene herein, the *Trichoderma reesei* cellobiohydrolase I gene (Shoemaker, S. P. et al. (1984) European Patent Application No. EP00137280A1), the *A. nidulans* trpC gene (Yelton, M. et al. (1984) *Proc. Natl. Acad. Sci. USA* 81, 1470–1474; Mullaney, E. J. et al. (1985) *Mol. Gen. Genet.* 199, 37–45) the *A. nidulans* alcA gene (Lockington, R. A. et al. (1986) Gene 33, 137–149), the *A. nidulans* tpiA gene (McKnight, G. L. et al. (1986) *Cell* 46, 143–147), the *A. nidulans* amdS gene (Hynes, M. J. et al. (1983) *Mol. Cell Biol.* 3, 1430–1439), and higher eukaryotic promoters such as the SV40 early promoter (Barclay, S. L. and E. Meller (1983) *Molecular and Cellular Biology* 3, 2117–2130).

Likewise a "terminator sequence" is a DNA sequence which is recognized by the expression host to terminate transcription. It is operably linked to the 3' end of the fusion DNA encoding the fusion polypeptide to be expressed. Examples include the terminator from the *A. nidulans* trpC gene (Yelton, M. et al. (1984) *Proc. Natl. Acad. Sci. USA* 81, 1470–1474; Mullaney, E. J. et al. (1985) *Mol. Gen. Genet.* 199, 37–45), the *A. awamori* or *A. niger* glucoamylase genes (Nunberg, J. H. et al. (1984) *Mol. Cell. Biol.* 4, 2306–253; Boel, E. et al. (1984) *EMBO J.* 3, 1581–1585), and the *Mucor miehei* carboxyl protease gene (EPO Publication No. 0 215 594), although any fungal terminator is likely to be functional in the present invention.

A "polyadenylation sequence" is a DNA sequence which when transcribed is recognized by the expression host to add polyadenosine residues to transcribed mRNA. It is operably linked to the 3' end of the fusion DNA encoding the fusion polypeptide to be expressed. Examples include polyadenylation sequences from the *A. nidulans* trpc gene (Yelton, M. et al. (1984) *Proc. Natl. Acad. Sci. USA* 81, 1470–1474; Mullaney, E. J. et al. (1985) *Mol. Gen. Genet.* 199, 37–45), the *A. awamori* or *A. niger* glucoamylase genes (Nunberg, J. H. et al. (1984) *Mol. Cell. Biol.* 4, 2306–2315) (Boel, E. et al. (1984) *EMBO J.* 3, 1581–1585), and the *Mucor miehei* carboxyl protease gene described above. Any fungal polyadenylation sequence, however, is likely to be functional in the present invention.

Materials and Methods

General methods were as previously described in EPO Publication 0 215 594.

Strains

The *Aspergillus awamori* strains used in this work were all derived from a glucoamylase over-producing strain (UVK143f), itself derived from NRRL3112 as described in EPO Publication No. 0 215 594. Strain genotypes were: strain GC12 (pyrG5; argB3) (derived from strain pyr4-5, also known as GC5, as described in U.S. patent application Ser. No. 214,237) and strain GCΔGAM23 (pyrG5; ΔglaA23).

Strain GCΔGAM23 was derived from strain GC12 by disruption of the glucoamylase (glaA) gene. This was achieved by transformation with a linear DNA fragment (similar to the method described by Miller et al. (1985) *Mol. Cell. Biol.* 5, 1714–1721) having glaA flanking sequences at either end and with 2.7 kb of the promoter and coding region of the glaA gene replaced by the *Aspergillus nidulans* argB gene as selectable marker. The vector from which we obtained this linear fragment of DNA was assembled as follows (FIG. 1). A 5.5 kb ClaI fragment of DNA containing approximately 3.5 kb of 5' flanking DNA and approximately 2 kb of coding sequence of the *A. awamori* UVK143f glaA gene was cloned into the ClaI site of pBR322. This plasmid was cut with restriction endonucleases XhoI and BglII to remove a section of DNA extending from a position 1966 bp upstream from the translation start codon to a position following approximately 200 codons of coding sequence. The overhanging DNA ends were filled in using the Klenow fragment of DNA polymerase I and ligated to reconstitute a BglII cleavage site and give pBRΔGAMXB. A 1.7 kb BamHI fragment containing the *Aspergillus nidulans* argB gene was cloned into this reconstituted BglII site to create the vector pBRΔgam-argB4 shown in FIG. 1. This vector was cut with ClaI and used to transform strain GC12 using complementation of the argB mutation to select for transformants. Integration of the linear fragment containing the glaA flanking sequences and the argB gene at the chromosomal glaA locus was identified by Southern blot analysis. Briefly, DNA from transformants and strain GC12 was digested with ClaI, subjected to agarose gel electrophoresis, transferred to a membrane filter and hybridized with a radiolabelled fragment of DNA containing the *A. niger* glaA gene. Two bands (5.5 and 1.9 kb in size) were observed in untransformed GC12 DNA following autoradiography representing the chromosomal glaA gene (data not shown). The predicted alteration due to disruption of the glaA gene was replacement of the 5.5 kb DNA fragment with a fragment of 4.5 kb (FIG. 2). This change had occurred in transformed strain GCΔGAM23. Enzyme immunoassays specific for glucoamylase confirmed that this strain did not secrete detectable levels of glucoamylase.

Media

Aspergillus complete and minimal media (Rowlands, R. T. et al. (1973) *Mol. Gen. Genet.* 126, 201–216) were used for the growth of fungal colonies and were supplemented with 2 mg/ml arginine or uridine as required. Two different liquid media were used to study chymosin production in shake flasks. SCM consisted of maltose, 50 g/l; malt extract, 20 g/l; yeast extract, 5 g/l; bacto-peptone, 1 g/l; arginine, 1 g/l; uridine, 1 g/l; methionine, 0.5 g/l; biotin, 2 mg/l; streptomycin, 50 mg/l; $KH_2PO_4$, 34 g/l; $NaNO_3$, 6 g/l; $MgSO_4.7H_2O$, 1 g/l; KCl, 0.52 g/l; trace elements solution (18), 1 ml/l; Tween-80, 1 ml/l; Mazu DF60-P antifoam (Mazur chemicals Inc.), 2 ml/l; pH5. Soy medium contained maltose, 150 g/l; soy bean meal or soluble soy-milk powder, 60 g/l; sodium citrate, 70 g/l; $(NH_4)_2SO_4$, 15 g/l; $NaH_2PO_4$, 1 g/l; $MgSO_4$, 1 g/l; Tween-80, 1 ml/l; Mazu DF60-P antifoam 2 ml/l; arginine 1 g/l; uridine, 1 g/l; streptomycin 50 mg/l; pH 6.2.

Fungal Transformation

Polyethylene glycol (PEG) mediated transformation was performed as described previously Cullen, D. et al. (1987) *Bio/Technology* 5, 369–376 except that 0.7 M KCl was used during preparation of protoplasts and was also added to the PEG solution. In addition, aurintricarboxylic acid (10 μg/ml) was added to the final protoplast wash prior to PEG treatment. We have observed that this nuclease inhibitor increased transformation frequencies for *A. awamori* by 2–5 fold and had little effect on protoplast viability (data not shown).

Transformation by electroporation was performed as described by Ward et al (1988) *Curr. Genet.* 14, 37–42. Briefly, washed protoplasts were suspended in electroporation buffer (7 mM sodium phosphate, pH 7.2, 1 mM $MgSO_4$, 1.4 M sorbitol), DNA was added and a pulse of 2,125 V/cm was delivered from the 25 μFD capacitor of a Bio-Rad Gene Pulser apparatus.

Following either method of transformation protoplasts were plated onto solidified Aspergillus minimal medium with 1.2 M sorbitol and lacking uridine.

DNA and RNA Manipulation

Standard methods were used for plasmid isolation, restriction enzyme digestion, ligation of DNA, DNA fragment isolation, DNA dephosphorylation, nick translation and Southern analysis (Maniatis, T. et al (1982) *Molecular Cloning. A Laboratory Manual,* Cold Spring Harbor Laboratory, Cold Spring Harbor, N.Y.). Fungal DNA was isolated as previously described (Cullen, D. et al (1982) *Bio/Technology* 5, 369–376).

Total RNA was extracted from fungi (24) and poly(A)$^+$ RNA was selected on oligo(dT) columns by standard procedures Maniatis (1982) supra. RNA was electrophoresed in formaldehyde-agarose gels prior to blotting to membrane filters for Northern analysis (Id.).

In vitro Translation

In vitro translation of poly(A)$^+$ RNA from *A. awamori* was done using rabbit reticulocyte lysates (Bethesda Research Laboratories, Gaithersberg, Md.). Each 60 µl reaction contained the following: 2.6 µl 2M potassium acetate, pH 7.2, 3 µl 20 mM magnesium acetate, pH 7.2, 10 µl (100 µCi) $^{35}$S-cysteine (Amersham, Arlington Heights, Ill.), 20 µl reaction buffer (Bethesda Research Laboratories, cat. no. 8112), 40 µl rabbit reticulocyte lysate (Bethesda Research Laboratories, cat. no. 8111), 36.8 µl of water and RNA (approximately 10 µg). The reactions were incubated at 30° C. for 60 minutes, then stopped by placing on ice. Incorporation of the $^{35}$S-cysteine was measured by precipitation with cold trichloroacetic acid (10% v/v).

Immunoprecipitation of radiolabelled chymosin polypeptides was done by the following method: 50 µl of $^{35}$S-labelled in vitro translation reaction was mixed with an equal volume of 2× NETS buffer (1× NETS buffer is 150 mM NaCl, 5 mM EDTA, 50 mM Tris-HCl, pH 7.4, 0.05% Triton X-100 and 0.25% gelatin). In order to remove proteins which non-specifically bind to protein A, 20 µl Pansorbin (protein A bearing *Staphylococcus aureus* cells; Calbiochem, La Jolla, Calif.) was added, mixed and incubated for 30 minutes at room temperature. The Pansorbin cells had previously been washed twice in 1× NETS and resuspended in their original volume (10% suspension). After incubating, the mixture was centrifuged and the supernatant was placed in a clean tube. Next 30 µl of chymosin antibody (purified by affinity chromatography and adjusted to a final concentration of 430 µg/ml in 1× NETS) was added and the mixture was incubated for 2 hours at room temperature. Following incubation, 50 µl of washed Pansorbin cells were added. The suspension was mixed thoroughly and incubated for 1 hour at room temperature. Subsequently, the mixture was centrifuged and the pellet was washed three times in 1× NETS. Lastly, the pellet was resuspended in 25 µl of water, mixed with an equal volume of sample buffer (1% SDS, 25 mM glycine, 192 mM Tris, pH 8.3, 50% sucrose, 50 mM β-mercaptoethanol) and heated to 95° C. for five minutes prior to SDS-polyacrylamide gel electrophoresis.

Chymosin Production by Transformants 50 ml of SCM or soy medium in 250 ml shake flasks were inoculated with fresh spore suspensions and cultured at 37° C. Samples were assayed for chymosin protein by enzyme immunoassay "EIA" Engvall, E. (1980) *Methods Enzymol* 70, 419–439 using rabbit anti-chymosin antibody and authentic calf chymosin (Chris Hansens Laboratorium, Denmark) as standard.

Chymosin activity assays were performed in microtitre plates and were based on an increase in turbidity due to milk clotting. 25 µl of sample was diluted in 10 mM sodium phosphate, pH 6.0 and 150 µl of substrate (1% skim milk, 40 mM $CaCl_2$ and 50 mM sodium acetate, pH 6.0) was added. After incubation at 37° C. for 15 min the turbidity was read at 690 nm. Authentic calf chymosin was used as the standard.

To determine intracellular chymosin concentrations mycelium was harvested from 50 ml cultures, washed thoroughly with water, freeze dried and ground in a mortar and pestle with sand. 50 ml of extraction buffer (50 mM sodium phosphate pH 5.5, 0.5 M NaCl, 1 mM phenyl methyl sulfonyl fluoride, 0.1 mM pepstatin) was added and mixed thoroughly. Samples of the extract were adjusted to 50 mM NaOH by the addition of 1 M NaOH, incubated at 37° C. for 30 min and finally centrifuged (13,000×g) to remove the cell debris. Chymosin concentration in the supernatant was measured by EIA.

For Western analysis samples were electrophoresed in SDS-polyacrylamide gels and blotted to membrane filters by standard procedures (Towbin, H. et al (1979) *Proc. Natl. Accad. Sci. u.s.a.* 76, 4350–4354). Blots were sequentially treated with rabbit anti-chymosin and goat anti-rabbit IgG conjugated with horse radish peroxidase (HRP). HRP color development was then performed by incubation with $H_2O_2$ and 4-chloro-1-napthol.

EXAMPLE 1

Increased Chymosin Secretion from A. awamori
Construction of pGAMpR

Construction of the chymosin expression vectors pGRG1 and pGRG3 has been described previously in Cullen, D. et al. (1987) *Bio/Technology* 5, 369–376 and EPO Publication No. 0 215 594. They consist of an expression cassette comprising an *A. niger* glaA promoter and terminator, either the glucoamylase or chymosin secretion signal, and the prochymosin B cDNA coding sequence. This cassette is present in pDJB3 (Ballance, D. J. et al. (1985) *Gene* 36, 321–331) which consists of pBR325, the *N. crassa* pyr4 gene and the ans1 sequence isolated from *A. nidulans* and conferring high transformation frequency in *A. nidulans* (FIG. 3). See also FIGS. 4A through 4D which depict the cassette inserts used to produce pGRG1 through pGRG4 respectively.

The vector pGAMpR contained prochymosin B cDNA sequences fused in frame to the last codon of the *A. awamori* glaA gene. Construction of this vector is outlined in FIGS. 5A and 5B. Briefly, a synthetic oligonucleotide (a 54 bp SalI-BamHI fragment encoding the last ten codons of glucoamylase and the first six codons of prochymosin) was cloned in an M13 vector and its nucleotide sequence verified. Into the same M13 vector we inserted a 235 bp BAMHI-Asp718 fragment from pR1 (Cullen (1987) supra and EPO Publication No. 0 215 594) comprising the 5' portion of the prochymosin coding sequence beginning at the seventh codon. From the resulting vector, designated M13mp19GAM3'-5'PR, a 280 bp SalI-Asp718 fragment was isolated and used in a three-part ligation with a 2.3 kb SalI-MluI fragment containing most of the *A. awamori* glucoamylase coding region plus 0.5 kb of 5' flanking DNA and an MluI-Asp718 vector fragment containing a pBR322 replicon, the 3' portion of prochymosin, the glucoamylase terminator region from *A. niger,* and a 1.4 kb segment (XhoI-MluI) of the *A. awamori* glucoamylase promoter region. The plasmid produced from this ligation, pBR-GAMpR, was digested with ClaI and ligated with a 2.1 kb ClaI fragment encoding the pyr4 gene from *Neurospora crassa* (Buxton, F. P. et al. (1983) *Mol. Gen. Genet.* 190, 403–405) to derive the final vector pGAMpR (FIGS. 5A and 5B).

Chymosin Production Levels

Protoplasts of strain GC12 and GCΔGAM23 were transformed, using PEG or electroporation, with plasmids pGRG1, pGRG3, and pGAMpR (FIGS. 3, 4A, 4C, 5A and 5B). These plasmids all included the N. crassa pyr4 gene which is capable of complementing the pyrG mutation of A. awamori, so allowing selection of transformants. Transformants with designations beginning with the number 12 are in strain GC12, those beginning with 23 are in GCΔGAM23. The name of the plasmid used for transformation is included in the designation. Following purification spores from the transformants were inoculated into 50 ml of SCM and cultured for 4 days. Replicate cultures of individual transformants were not performed and no attempt was made to correct for different growth rates. Immunoassays were performed on the culture supernatants and on intracellular extracts of the mycelium (Table 1). Treatment of the intracellular extract with NaOH was required to release chymosin from the insoluble cellular debris. However, this treatment was also found to decrease the amount of detectable chymosin in standard samples using EIA by approximately 25%. Thus, the values recorded in Table 1 for intracellular chymosin are underestimates.

TABLE I

Table 1. Concentration of chymosin in samples from 4 day old SCM cultures

| | Chymosin Concentration (μg/ml) | | |
|---|---|---|---|
| Strain | Intra-cellular | Extra-cellular | % Intra-cellular |
| GC12 | N.D. | N.D. | |
| GCΔGAM23 | N.D. | N.D. | |
| 12grg1-1 | 5.4 | 1.2 | 81.8 |
| 12grg1-1a | 20.8 | 0.5 | 97.7 |
| 12grg1-3a | 0.6 | 1.1 | 35.3 |
| 12grg1-4a | 2.5 | 1.4 | 64.1 |
| 12grg1-5a | 4.6 | 0.8 | 85.2 |
| 12grg3-3a | 2.5 | 3.7 | 40.3 |
| 12grg3-5a | 6.0 | 0.9 | 87.0 |
| 12grg3-6a | 1.7 | 1.2 | 58.6 |
| 12grg3-7a | 1.5 | 1.3 | 53.6 |
| 12grg3-9a | 0.8 | 3.2 | 20.0 |
| 23grg1-1a | 4.4 | 1.4 | 75.9 |
| 23grg1-2a | 20.1 | 0.6 | 97.1 |
| 23grg1-3a | 4.1 | 0.7 | 85.4 |
| 23grg1-5a | 5.4 | 0.8 | 87.1 |
| 23grg3-1a | 9.2 | 0.1 | 98.9 |
| 23grg3-2a | 8.1 | 0.4 | 95.3 |
| 23grg3-3a | 20.8 | 0.2 | 99.0 |
| 23grg3-6a | 2.7 | 0.6 | 81.8 |
| 23grg3-7a | N.D. | 0.1 | 0.0 |
| 12gampr1 | 0.3 | 0.7 | 30.0 |
| 12gampr2 | 0.5 | 4.3 | 10.4 |
| 12gampr3 | N.D. | 1.2 | 0.0 |
| 12gampr4 | 2.0 | 33.6 | 5.6 |
| 12gampr31[a] | 0.6 | 26.6 | 2.2 |
| 12gampr58[a] | 0.8 | 24.9 | 3.1 |
| 23gampr1 | 0.3 | 2.0 | 13.0 |
| 23gampr3 | N.D. | 0.2 | 0.0 |
| 23gampr4 | 0.6 | 47.5 | 1.2 |
| 23gampr5 | 0.3 | 41.5 | 0.7 |
| 23gampr6 | 0.1 | 19.7 | 0.5 |
| 23gampr7 | 0.8 | 42.7 | 1.8 |

N.D.: not detected;
[a]transformants selected as high producers.

None of the pGRG1 or pGRG3 transformants, expected to synthesize preprochymosin without fusion to glucoamylase, gave levels of secreted chymosin greater than 3.7 μg/ml. As noted previously using strain GC5 (see U.S. patent application Ser. No. 214,237, abandoned) many of the pGRG1 and pGRG3 transformants had high intracellular levels of chymosin, with greater than 75% of the total chymosin produced remaining within the cell in many of the transformants. In contrast, several of the pGAMpR transformants secreted comparatively high levels of chymosin and in the majority of cases the intracellular levels of chymosin were much lower than the amounts of secreted chymosin. At this time it was noted that higher expression levels could be obtained in soy medium, possibly related to the higher pH of this medium which might reduce the activity of native, secreted aspartyl proteases. Strains 12grg1-1a, 12gampr4 and 23gampr46 (not shown in Table 1) were chosen as the highest producers for further study. The levels of intracellular and extracellular chymosin produced by triplicate, 6 day old, 50 ml Soy bean meal medium cultures of these strains were measured by EIA and activity assays. In addition, glucoamylase concentrations in the culture supernatants were measured by EIA (Table II).

TABLE II

Table 2 Chymosin and glucoamylase production by transformants expressed as milligrams per gram dry weight of mycelium.

| Transformant | Chymosin Activity | Extra-cellular Chymosin EIA | Glyco-amylase EIA | Intra-cellular Chymosin EIA |
|---|---|---|---|---|
| 12grg1-1a | 1.0 | 1.3 | 64.1 | 0.6 |
| 12gampr4 | 22.0 | 27.7 | 146.0 | 0.0 |
| 23gampr46 | 14.3 | 21.7 | 59.1 | 0.7 |

In all cases the amount of secreted chymosin detected by EIA was greater than that detected by activity assays. This may reflect the presence of inactive or degraded chymosin molecules. The results confirmed the high levels of secreted chymosin produced by transformants expressing chymosin as a fusion protein. Approximately 140 μg of active chymosin was secreted per ml of culture by transformant 12gampr4 compared to approximately 8 μg/ml for 12grg1-1a.

The only glucoamylase produced by transformant 23gampr46 (deleted for the native glaA gene) would be as part of the glucoamylase-chymosin fusion protein. Since the sizes of the two forms of glucoamylase (MW 61,000 and 71,000) are approximately twice that of chymosin (MW 37,000) one would expect double the amount, by weight, of glucoamylase to be secreted compared to chymosin. In fact, the measured ratio of glucoamylase to chymosin in the culture medium was closer to 3:1. This discrepancy may be due to inaccuracies in the assays or may indicate that degradation of chymosin has occurred. In transformant 12grg1-1a only native glucoamylase would be produced whereas in 12gampr4 both native and chymosin-associated glucoamylase would be secreted. Interestingly, almost as much recombinant glucoamylase was produced in 23gampr46 as native glucoamylase in 12grg1-1a. Although a high percentage (32%) of the total amount of chymosin produced by 12grg1-1a remained within the cell this was not nearly as dramatic as the intracellular accumulation observed in SCM culture.

Southern Blot Analysis

DNA was extracted from strains GC12 and GCΔGAM23 and from transformants 12gampr2, 12gampr3, 12gampr4, 23gampr1 and 23gampr46, digested with XhoI and HindIII, and subjected to electrophoresis. After blotting onto membrane filters the DNA was hybridized with radiolabelled pGAMpR (FIG. 8). For strain GC12 a single band representing the native glaA gene was observed (FIG. 8, Lane a).

A smaller sized glaA fragment was seen in strain GCΔGAM23 due to the gene replacement event at this locus (FIG. 8, Lane e). The plasmid pGAMpR was also run on the gel to show the size of fragments obtained from this on digestion with XhoI and HindIII (FIG. 8, Lane h). Additional bands derived from pGAMpR were observed in the transformants. For 12gampr4 and 23gampr1 the pattern was consistent with the integration of a few tandem copies of pGAMpR at a single site away from the glaA locus (FIG. 8, lanes d and f). The number of plasmid copies in these transformants appears to be similar despite the large differences in chymosin productivity. Although tandem plasmid integration has probably occurred more extensive plasmid rearrangements were also involved in transformants 12gampr2, 12gampr3 and 23gampr46 (FIG. 8, lanes b, c and g).

Northern Analysis

Total RNA was extracted from strains GC12, 12grg1-1a and 12gampr4 subjected to electrophoresis and blotted to membrane filters. The RNA was then hybridized simultaneously with two radiolabelled DNA probes (FIG. 9). One of these probes was a 5 kb EcoR1 fragment containing the *A. niger* olic gene (Ward et al (1988) Curr. Genet. 14, 37–42) to act as an internal control demonstrating that equivalent amounts of the different RNA samples were applied to the gel and that none of the samples was excessively degraded. The second probe was an approximately 850 bp KpnI-BclI fragment of chymosin coding sequence. In addition to the oliC mRNA band of approximately 1 kb a 1.4 kb band representing chymosin mRNA was observed in transformant 12grg1-1a (FIG. 9, lane b). It was apparent that abundant chymosin-specific message was present in this transformant although the level of chymosin production was very much lower than glucoamylase production (this strain is capable of secreting approximately 0.8 gm/l of glucoamylase). A mRNA species of the size expected for a fused glucoamylase-chymosin message (3.4 kb) was observed in strain 12gampr4 (FIG. 9, lane c). This fused mRNA species appeared to be less abundant than the chymosin-specific mRNA present in transformant 12grg1-1a even though chymosin production was much greater in transformant 12gampr4. Only the olic mRNA was observed in strain GC12 (FIG. 9, lane a).

In vitro Translation

Polyadenylated RNA samples isolated from cultures of transformants 12gampr4, 23gamp46 and 12grg1-1a were translated in a commercial rabbit reticulocyte in vitro translation system. Chymosin was immunoprecipitated from the translation products, subjected to SDS-polyacrylamide gel electrophoresis and visualized by autoradiography (FIG. 10). Two distinct bands, representing proteins of MW 37,000 and 42,000, were observed with mRNA from 12grg1-1a (FIG. 10, lane b) which was expected to produce only preprochymosin (MW 42,000). The lower MW species may represent mature chymosin although autocatalytic processing would not be expected to take place at the pH at which the translation reactions were performed. With 12gampr4 (FIG. 10, lane a) and 23gampr46 mRNA samples two high MW species were precipitated with the anti-chymosin antibody. These were of the approximate size expected for full-length fusion proteins (100,000 and 110,000 MW) containing prochymosin and either one or the other of the two forms of glucoamylase. No chymosin could be immunoprecipitated if GC12 RNA (FIG. 10, lane c) or no RNA (FIG. 10, lane d) was added to the in vitro translation system.

Western Analysis

Supernatants were collected from 50 ml SCM or soy medium cultures of transformants 12gampr4, 23gampr46 and 12grg1-1a at various time points after inoculation. Samples were separated by SDS-polyacrylamide gel electrophoresis, blotted to membrane filters and probed with antibody specific for chymosin (FIG. 11). No chymosin was observed in the culture supernatant from strain GC12 (FIG. 11, lane b). Authentic bovine chymosin was also run on the gel (FIG. 11, lanes a and i). A band of the same size as authentic bovine chymosin (37,000 MW) was observed in all the samples from SCM cultures of 2 days and older. In soy medium cultures of 12gampr4 (FIG. 11, lane g) and 23gampr46 an additional band of approximately the size expected (100,000 MW) for a full-length glucoamylase-chymosin fusion protein was evident at 2 and 3 days although this was diminished at later time points. The major chymosin-specific band present in samples from 12grg1-1a cultures in soy medium at 2 days was of the size predicted for prochymosin (FIG. 11, lane d). Soy medum was buffered at pH 6.2, whereas SCM medium was at pH 5. At the higher pH activation of prochymosin would be expected to be slow.

The pH of samples from day 2 or 3 soy medium cultures was lowered to pH 2 for 30 min. at room temperature. The pH was then raised immediately to above pH 6 before loading the sample onto an SDS polyacrylamide gel for Western analysis. This treatment led to a loss of the large molecular weight band from 12gampr4 (FIG. 11, lane h) or 23gampr46 or loss of prochymosin from 12grg1-1a (FIG. 11, lane e) and the accumulation of a protein species slightly larger than mature chymosin, possibly pseudochymosin in all transformants. These changes in the size of chymosin-specific bands were inhibited if the aspartyl protease inhibitor pepstatin (Marciniszyn, J. Jr. et al. (1976) *J. Biol. Chem.* 251, 7095–7102) was included at 0.1 mM during the low pH treatment. Chymosin concentration measured by activity assays on samples from 2 day old soy medium cultures of 12grg1-1a and 23gampr46 were 0.7 and 3.2 µg/ml respectively before treatment at pH 2. Following treatment these values rose to 3.6 and 17.5 µg/ml respectively, an increase of approximately 5 fold in each case.

As can be seen from Tables I and II, the yields of secreted chymosin in *A. awamori* are greatly enhanced if prochymosin is synthesized as a fusion with the carboxyl terminus of glucoamylase as compared to direct expression from the glaA promoter utilizing the glucoamylase signal peptide. Increased efficiency of secretion of the fusion protein compared to prochymosin appears to be at least part of the explanation for higher expression levels. This is apparent from the high proportion of chymosin found within the cell in pGRG1 and pGRG3 transformants compared to pGAMpR transformants. Neither authentic bovine chymosin, nor the majority of the chymosin produced in *A. awamori* are glycosylated. Attachment of prochymosin to glucoamylase, which is extensively decorated with O-linked carbohydrates in *A. niger* (Pazur, J. H. et al. (1987) *J. Protein Chem.* 6, 517–527), may allow more efficient passage through the Aspergillus secretory pathway.

The plasmids pGRG1 and pGRG3 both employ an *A. niger* glaA promoter to direct chymosin expression, whereas an *A. awamori* glaA promoter is present in pGAMpR. There are additional differences between these plasmids such as the inclusion of the ans1 sequence on pGRG1 and pGRG3. Integration of the various plasmids was probably not by homology with the native glaA locus. Consequently, the chromosomal location of the integrated plasmids was presumably different in each transformant. All of these differences make it difficult to compare the total amounts of chymosin produced (intracellular plus extracellular) and to determine if this is similar between transformants, with the distribution between the inside and the outside of the cell being the only distinction between direct expression and production as a fusion protein. Northern analysis suggested that the steady state level of chymosin-specific mRNA were higher in transformant 12grg1-1a than in 12gampr4, making some comparison of chymosin yields valid.

Analysis of the total amount of chymosin produced by transformants 12grg1-1a, 12gampr4 and 23gampr46 in soy medium showed that the total amount of chymosin produced in the direct expression transformant was much less than that in the transformants expressing chymosin as a fusion protein. This might suggest that enhanced efficiency of secretion may not be the only benefit of expression of chymosin fused to glucoamylase. It is possible that translation of the glucoamylase-chymosin fusion mRNA was more efficient than translation of prochymosin mRNA in which only the untranslated leader sequence and the secretion signal sequence was derived from the glaA gene. However, it may be difficult to get an accurate value for intracellular chymosin levels since extraction may not be complete and the NaOH treatment required to release chymosin reduced detection by EIA. Additionally, chymosin which accumulates intracellularly may be subject to degradation by native proteases prior to extraction. Consequently, the figures obtained for intracellular chymosin concentrations will always be underestimates.

It was apparent, using samples from young cultures in soy bean meal medium at pH 6, that a large proportion of the glucoamylase-prochymosin fusion protein was secreted to the medium intact, although some mature chymosin was also observed. Under these conditions prochymosin was the only form detected by Western analysis of samples from the direct expression transformant 12grg1-1a. In contrast, only mature chymosin was detected in cultures of any of the transformants in SCM at pH 5. These observations suggested that the release of chymosin from the glucoamylase-chymosin fusion protein was favored at low pH and may involve the natural autocatalytic activation mechanism of prochymosin. Loss of the fusion protein and an increase in active chymosin concentration could be induced simply by lowering the pH of samples to 2. As might be expected if processing was dependent on chymosin activity, at least some of the chymosin released from the fusion protein under these conditions appeared to be in the form of pseudochymosin. Presumably, this would eventually be further processed to mature chymosin under the appropriate conditions. Processing of the fusion protein at pH 2 was inhibited by pepstatin suggesting that it required the activity of an aspartyl protease. This activity could be supplied by chymosin itself or by a native A. awamori protease. We have constructed a strain of A. awamori in which the gene encoding the major secreted aspartyl protease, aspergillopepsin A, has been deleted (see U.S. patent application Ser. No. 214,237, abandoned). Although there is a low level of extracellular proteolytic activity remaining in this strain, this activity is unaffected by pepstatin. Processing of the glucoamylase-chymosin fusion in this aspergillopepsin-deleted strain is indistinguishable from the processing described above for transformants 12gampr4 and 23gampr46 (data not shown). This is further indication that the pepstatin-inhibitable activity which causes processing of the fusion protein is actually that of chymosin itself.

Amino terminal sequencing of the mature chymosin obtained from pGAMpR transformants has confirmed that correct processing has occurred (results not shown). Other tests, including amino acid composition analysis, specific activity determination, Ouchterlony plate tests and cheese-making trials, have confirmed the authenticity of the chymosin produced in these transformants.

EXAMPLE 2

Secretion of Chymosin from a Fusion Polypeptide Containing A. awamori α-amylase

Construction of pAMpRI and pAMpRII

Aspergillus awamori strain UVK143f has two almost identical α-amylase genes (amyA and amyB), both of which had been cloned and one of which has been sequenced (Korman, D. R., (1988). The cloning and characterization of α-amylase genes of Aspergillus oryzae and Aspergillus awamori. MA thesis, San Fransisco State University). Subsequently, the second gene has been sequenced. The amyA gene encodes a protein of 496 amino acids including an amino terminal signal sequence of 21 amino acids. The sequence for each of the two genes is identical, including 200 bp of sequence 5' to the translation start codon, the position and sequence of the eight introns and the entire coding sequence except for the sequence encoding the final two or three carboxyl terminal amino acids (codons for tyrosine and glycine in amyA are replaced by three serine codons in amyB). The vectors pUCAMpRI and pUCAMpRII contain similar prochymosin B expression cassettes to pGAMpR except that the promoter, the entire coding sequence of the A. awamori amyA or amyB genes and the amyA terminator and polyadenylation sequence replace those of the glaA gene.

Construction of pUCAMpRI is described in FIG. 6. Briefly, a synthetic oligonucleotide encoding the last five amino acids of α-amylase (amyA version) and the first six amino acids of prochymosin was used to link exactly and in frame a BamHI-Asp718 fragment encoding a region of the prochymosin B coding sequence starting at the seventh codon with a BglI-HindIII fragment encoding the promoter region (up to 617 bp 5' of the translation start codon) and all of the coding sequence of amyA up to the sixth codon prior to the translation stop codon (pUCAMYint. #2). The remaining portion of the chymosin coding sequence was added as an Asp718-XbaI fragment taken from a GRG1 type expression cassette to give pUCAMYint. #3 (i.e., the XbaI site 11 bp after the translation stop codon being an engineered site introduced during construction of pGRG1). Site directed mutagenesis was used to introduce an XbaI site 11 bp after the translation stop codon of the amyA gene so that the terminator and polyadenylation region (581 bp) from this gene could be placed immediately after the prochymosin sequence in pUCAMYint. #3 to give pUCAMpR1. The vector pUCAMpRII was essentially the same except that the amyA promoter was exchanged for the corresponding region of the amyB gene.

Secretion of Chymosin

The plasmids pUCAMpRI and pUCAMpRII contain no gene which could be used as a selectable marker for transformation into filamentous fungi. It was therefore necessary to introduce these plasmids into A. awamori by cotransformation with a second plasmid which did contain a selectable marker. Consequently approximately 10 μg of pUCAMpRI or pUCAMpRII was mixed with approximately 2 μg of pBH2 (pUC18 with a 2.4 kb BamHI-HindIII fragment containing the Asperaillus niger pyrG gene) and used to transform strain ΔAP3 (described in U.S. patent application Ser. No. 214,237, abandoned) using complementation of the pyrG mutation in this strain as a selection system for transformants. A proportion of the transformants obtained in this manner should contain both plasmids. Individual transformants were subsequently grown in 1 ml liquid cultures in 24 well microtiter plates and the culture supernatants assayed for chymosin activity. Those transformants which produced the greatest amount of active, secreted chymosin were then grown in 50 ml shake flask cultures in soy bean meal medium for further analysis. The greatest amount of chymosin produced by transformants of strain ΔAP3 was similar regardless of whether pUCAMpRI or pUCAMpRII was used for transformation. The maximum production observed was 70–80 μg/ml of chymosin. This is higher than the level of production expected if the preprochymosin had been fused directly to the α-amylase promoter without inclusion of the α-amylase coding sequence. Western immunoblotting analysis of culture supernatants using anti-chymosin antibodies for specific staining showed that, as with pGAMpR transformants, a fusion protein could be observed in addition to a band the size of mature chymosin (37,000 MW). The fusion protein was of the expected size (91,000 MW) for a full length α-amylase/prochymosin fusion polypeptide and could also be identified using anti-α-amylase antibody for specific staining. Mature chymosin was released from the α-amylase/prochymosin fusion protein at low pH as was observed for the glucoamylase/prochymosin fusion protein.

EXAMPLE 3

Construction of pSG1

In order to test if enhanced chymosin production and secretion could be achieved by fusing a smaller part of the glucoamylase polypeptide sequence to the amino terminus of prochymosin a vector, pSG1, was constructed (FIG. 7). The starting point for this plasmid construction was a vector (pUCAagrg4) containing a XhoI/HindIII glucoamylase/chymosin expression cassette (promoter, coding sequence and terminator regions) identical to that in pGRG4 (see EPO Publication No. 0 215 594) except that the *Aspergillus awamori* UVK143f glaA promoter, signal sequence, prosequence and first 11 codons of the mature coding sequence replaced the equivalent region from the *A. niger* glaA gene. This expression cassette was inserted between the HindIII and SalI sites of pUC18 (Yanisch-Peron, et al., 1985, Gene 33, 103–119). From pUCAagrg4 we isolated a 2.3 kb Asp718 fragment containing the *A. awamori* UVK143f glaA promoter, signal sequence, prosequence and first 11 codons of the mature glucoamylase coding sequence as well as an amino terminal portion of the prochymosin coding sequence. This fragment was cloned into the Asp718 restriction site of pUC18 to give pUCgrg4X/K. A 1 kb BssHII fragment from the coding sequence (from within the prosequence to a point approximately half way through the mature coding sequence) of the *A. awamori* glaA gene was inserted into the unique BssHII site in the glaA prosequence region of pUCgrg4X/K to give pUCgrg4X/K+B. Finally, we isolated the larger Asp718 fragment from pUCAagrg4, containing the pUC replicon, the 3' end of the chymosin coding sequence and the *A. niger* glaA polyadenylation and termination region and ligated this with the larger Asp718 fragment from pUCgrg4X/K+B to give pSG1. The glucoamylase/prochymosin polypeptide expected to be produced as a result of transcription and translation should consist of glucoamylase signal sequence, glucoamylase prosequence, amino acids 1–297 of mature glucoamylase followed immediately by amino acids 1–11 of mature glucoamylase and finally prochymosin at the carboxyl terminus.

We have used pSG1 in cotransformation experiments with pBH2 but have failed to identify transformants which produce active chymosin. The reason for this is unclear and further work is in progress to clarify the situation. It may be that the glucoamylase/prochymosin fusion polypeptide encoded by this plasmid is not secreted efficiently, or mature, active chymosin may not be released from the fusion polypeptide. However, it is also conceivable that the plasmid was not constructed as predicted, or that transcription or translation of the glucoamylase/chymosin coding sequences were not efficient.

The foregoing are presented by way of example only and should not be construed as a limitation to the scope of permissible claims.

Having described the preferred embodiments of the present invention, it would appear to those ordinarily skilled in the art that various modifications may be made to the disclosed embodiments, and that such modifications are intended to be within the scope of the present invention.

All references are expressly incorporated herein by reference.

What is claimed is:

1. A fusion DNA sequence encoding a fusion polypeptide comprising, from the 5' end of said fusion DNA sequence, first, second, third and fourth DNA sequences encoding, from the amino- to carboxy-terminus of said fusion polypeptide, corresponding first, second, third and fourth amino acid sequences, said first DNA sequence encoding a signal peptide functional as a secretory sequence in a first filamentous fungus, said second DNA sequence encoding a secreted polypeptide or portion thereof, said third DNA sequence encoding a cleavable linker polypeptide and said fourth DNA sequence encoding a desired polypeptide, wherein the expression of said fusion DNA sequence in said first filamentous fungus or in a second filamentous fungus results in increased secretion of said desired polypeptide as compared to the secretion of said desired polypeptide from said first or said second filamentous fungus when expressed as a second fusion polypeptide encoded by a second fusion DNA sequence comprising only said first, third and fourth DNA sequences.

2. The fusion DNA sequence of claim 1 wherein said first DNA sequence encodes a signal peptide selected from the group consisting of signal peptides from glucoamylase, α-amylase, and aspartyl protease from Aspergillus species, signal peptides from bovine chymosin and human tissue plasminogen activator and signal peptides from Trichoderma cellobiohydrolase I and II.

3. The fusion DNA sequence of claim 1 wherein said first DNA sequence encodes the signal peptide from *Asperaillus awamori* glucoamylase.

4. The fusion DNA sequence of claim 1 wherein said second DNA sequence encodes a secreted polypeptide or a portion thereof selected from the group consisting of glucoamylase, α-amylase, and aspartyl protease from Aspergillus species and Trichoderma cellobiohydrolase I and II.

5. The fusion DNA sequence of claim 1 wherein said second DNA sequence encodes glucoamylase from *Aspergillus awamori* or a portion thereof.

6. The fusion DNA sequence of claim 1 wherein said third DNA sequence encodes a cleavable linker polypeptide selected from the group consisting of the prosequence from chymosin, the prosequence of subtilisin, and sequences recognized by trypsin factor $X_a$, collagenase, clostripain, subtilisin and chymosin.

7. The DNA sequence of claim 1 wherein said third DNA sequence encodes the prosequence of chymosin or a portion thereof.

8. The fusion DNA sequence of claim 1 wherein said fourth DNA sequence encodes a desired polypeptide selected from the group consisting of enzymes, proteinaceous hormones and serum proteins.

9. The fusion DNA sequence of claim 1 wherein said fourth DNA sequence encodes bovine chymosin.

10. The fusion DNA sequence of claim 1 wherein said first DNA sequence encodes the signal peptide from *Aspergillus awamori* glucoamylase, said second sequence encodes glucoamylase from *Aspergillus awamori* said third sequence encodes the prosequence of chymosin and said fourth sequence encodes chymosin.

11. An expression vector for transforming a host filamentous fungus comprising DNA sequences encoding regulatory sequences functionally recognized by said host filamentous fungus including promoter and transcription and translation initiation sequences operably linked to the 5' end of the fusion DNA sequence of claim 1 and transcription stop sequences and polyadenylation sequences operably linked to the 3' end of said fusion DNA sequence.

12. The expression vector of claim 11 wherein said first and said second DNA sequences encoding respectively said signal peptide and said secreted polypeptide are selected from filamentous fungi of the same genus as said host filamentous fungus.

13. The expression vector of claim 12 wherein said genus is selected from the group consisting of Aspergillus, Trichoderma, Neurospora, Penicillium, Cephalosporium, Podospora, Endothia, Mucor, Cochliobolus, Pyricularia, Achlya and Humicola.

14. The expression vector of claim 12 wherein said genus is Aspergillus.

15. The expression vector of claim 11 wherein said first and said second DNA sequences encoding respectively said signal peptide and said secreted polypeptide are from said host filamentous fungus.

16. A filamentous fungus comprising an expression vector, said expression vector as in one of claims 11–15.

17. A fusion polypeptide comprising, from the amino- to carboxy-terminus, first, second, third and fourth amino acid sequences, said first amino acid sequence comprising a signal peptide functional as a secretory sequence in a first filamentous fungus, said second amino acid sequence comprising a secreted polypeptide or portion thereof, said third amino acid sequence comprising a cleavable linker polypeptide and said fourth amino acid sequence comprising a desired polypeptide, wherein the expression of a fusion DNA sequence encoding said fusion polypeptide in said first filamentous fungus or in a second filamentous fungus results in increased secretion of said desired polypeptide as compared to the secretion of said desired polypeptide from said first or said second filamentous fungus when expressed from a second fusion DNA sequence encoding a second fusion polypeptide comprising only said first, third and fourth amino acid sequences.

18. The fusion polypeptide of claim 17 wherein said first amino acid sequence comprises a signal peptide selected from the group consisting of signal peptides from glucoamylase, α-amylase, and aspartyl protease from Aspergillus species, signal peptides from bovine chymosin and human tissue plasminogen activator and signal peptides from Trichoderma cellobiohydrolase I and II.

19. The fusion polypeptide of claim 17 wherein said first amino acid sequence is the signal peptide from *Asperaillus awamori* glucoamylase.

20. The fusion polypeptide of claim 17 wherein said second amino acid sequence is selected from the group consisting of glucoamylase, α-amylase, and aspartyl protease from Aspergillus species and Trichoderma cellobiohydrolase I and II.

21. The fusion polypeptide of claim 17 wherein said second amino acid sequence is glucoamylase from *Aspergillus awamori*.

22. The fusion polypeptide of claim 1 wherein said cleavable linker polypeptide is selected from the group consisting of the prosequence of subtilisin, and sequences recognized by trypsin factor $X_a$, collagenase, clostripain, subtilisin and chymosin.

23. The fusion polypeptide of claim 17 wherein said third amino acid sequence is the prosequence of chymosin.

24. The fusion polypeptide of claim 17 wherein said fourth amino acid sequence is selected from the group consisting of enzymes, proteinaceous hormones and serum proteins.

25. The fusion polypeptide of claim 17 wherein said fourth amino acid sequence is chymosin.

26. The fusion polypeptide of claim 17 wherein said first amino acid sequence is the signal peptide of *A. awamori* glucoamylase, said third amino acid sequence is the prosequence of chymosin and said fourth amino acid sequence is bovine chymosin.

27. A process for producing a desired polypeptide comprising:
culturing a host filamentous fungus transformed with an expression vector comprising the fusion DNA sequence of claim 1 under conditions which permit expression of said fusion DNA sequence to cause the secretion of the desired polypeptide encoded by said fusion DNA sequence.

28. A process according to claim 27, wherein said first DNA sequence encodes a signal peptide selected from the group consisting of signal peptides from glucoamylase, α-amylase, and aspartyl protease from Aspergillus species, signal peptides from bovine chymosin and human tissue plasminogen activator and signal peptides from Trichoderma cellobiohydrolase I and II.

29. A process according to claim 27, wherein said first DNA sequence encodes a signal peptide from *Aspergillus awamori* glucoamylase.

30. A process according to claim 27, wherein said second DNA sequence encodes a secreted polypeptide or a portion thereof selected from the group consisting of glucoamylase, α-amylase, and aspartyl protease from Aspergillus species and Trichoderma cellobiohydrolase I and II.

31. A process according to claim 27, wherein said second DNA sequence encodes glucoamylase from *Aspergillus awamori* or a portion thereof.

32. A process according to claim 27, wherein said third DNA sequence encodes a cleavable linker polypeptide selected from the group consisting of the prosequence from chymosin, the prosequence of subtilisin, and sequences recognized by trypsin factor $X_a$, collagenase, clostripain, subtilisin and chymosin.

33. A process according to claim 27, wherein said third DNA sequence encodes the prosequence of chymosin or a portion thereof.

34. A process according to claim 27, wherein said fourth DNA sequence encodes a desired polypeptide selected from the group consisting of enzymes, proteinaceous hormones and serum proteins.

35. A process according to claim 27, wherein said fourth DNA sequence encodes bovine chymosin.

36. A process according to claim 27, wherein said first DNA sequence encodes the signal peptide from *Aspergillus awamori* glucoamylase, said second sequence encodes glucoamylase from *Aspergillus awamori,* said third sequence encodes the prosequence of chymosin and said fourth sequence encodes chymosin.

37. A process according to claim 27, wherein said expression vector comprises DNA sequences encoding regulatory sequences functionally recognized by said host filamentous fungus including promoter and transcription and translation initiation sequences operably linked to the 5' end of said fusion DNA sequence and transcription stop sequences and polyadenylation sequences operably linked to the 3' end of said fusion DNA sequence.

38. A process according to claim 27, wherein said signal peptide and said secreted polypeptide are selected from filamentous fungi of the same genus as said host filamentous fungus.

39. A process according to claim 38, wherein said genus is selected from the group consisting of Aspergillus, Trichoderma, Neurospora, Penicillium, Cephalosporium, Podospora, Endothia, Mucor, Cochliobolus, Pyricularia, Achlya and Humicola.

40. A process according to claim 38, wherein said genus is Aspergillus.

41. A process according to claim 38, wherein said first and said second DNA sequences encoding respectively said signal peptide and said secreted polypeptide are from said host filamentous fungus.

* * * * *